United States Patent
Yossepowitch et al.

(10) Patent No.: US 8,002,780 B2
(45) Date of Patent: Aug. 23, 2011

(54) ASSISTED APPARATUS FOR ANASTOMOSIS AND METHOD THEREBY OF RECONNECTING THE URETHRA TO THE BLADDER AFTER REMOVAL OF THE PROSTATE DURING A PROSTATECTOMY

(75) Inventors: Ofer Yossepowitch, Petach Tikva (IL); Eliahu Eliachar, Haifa (IL); Nir Lilach, Kfar Yehoshua (IL); Dan Sade Hochstadter, Kibbutz Bet Alfa (IL); Eyal Bressler, Almon (IL)

(73) Assignee: Keren Medical Ltd., Kibbutz Bet Alfa, IL (US)

( * ) Notice: Subject to any disclaimer, the term of this patent is extended or adjusted under 35 U.S.C. 154(b) by 697 days.

(21) Appl. No.: 11/995,635

(22) PCT Filed: May 21, 2006

(86) PCT No.: PCT/IL2006/000595
§ 371 (c)(1),
(2), (4) Date: Jan. 14, 2008

(87) PCT Pub. No.: WO2006/123348
PCT Pub. Date: Nov. 23, 2006

(65) Prior Publication Data
US 2008/0275472 A1   Nov. 6, 2008

Related U.S. Application Data

(60) Provisional application No. 60/682,373, filed on May 19, 2005.

(51) Int. Cl.
*A61B 17/12* (2006.01)
(52) U.S. Cl. ...................................................... 606/144
(58) Field of Classification Search .................. 606/139, 606/144, 151, 153
See application file for complete search history.

(56) References Cited

U.S. PATENT DOCUMENTS 4,553,543 A * 11/1985 Amarasinghe ................ 606/148
2004/0087995 A1   5/2004 Copa et al.

OTHER PUBLICATIONS

International Preliminary Report on Patentability published Mar. 31, 2009 for PCT/IL2006/000595 filed May 21, 2006.

* cited by examiner

*Primary Examiner* — Darwin P Erezo
*Assistant Examiner* — Gregory Anderson
(74) *Attorney, Agent, or Firm* — Martin Fleit; Paul D. Bianco; Fleit Gibbons Gutman Bongini & Bianco PL

(57) ABSTRACT

An assisted anastomosis apparatus and a method thereby for reconnecting the urethral stump to the neck of the bladder after removal of the prostate during a prostatectomy, comprising two suture units, namely a urethral stump suturing unit (1a) and a bladder suturing unit (1b), at least a section of said urethral stump suturing unit (1a) has suitable dimensions to be introduced into a bladder neck and at least a section of said bladder suturing unit (1b) has suitable dimensions to be introduced into a urethral stump; such that each needle pulls the suture leading from its equivalent position on the urethral stump through the wall of the bladder neck.

5 Claims, 25 Drawing Sheets

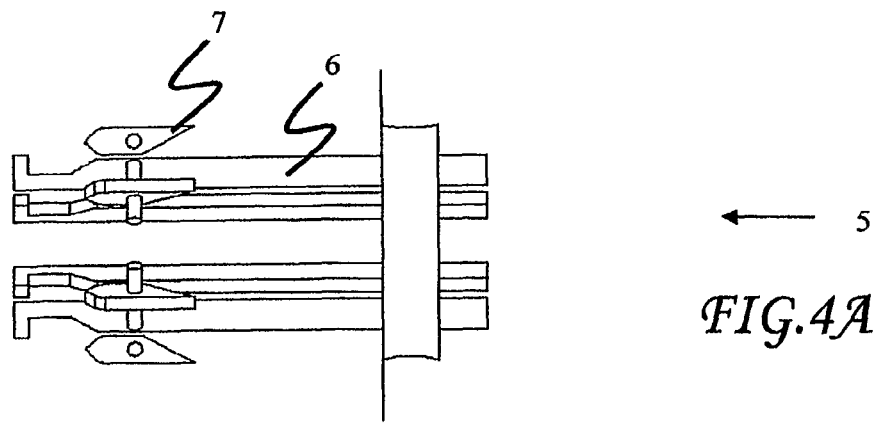
FIG.4A
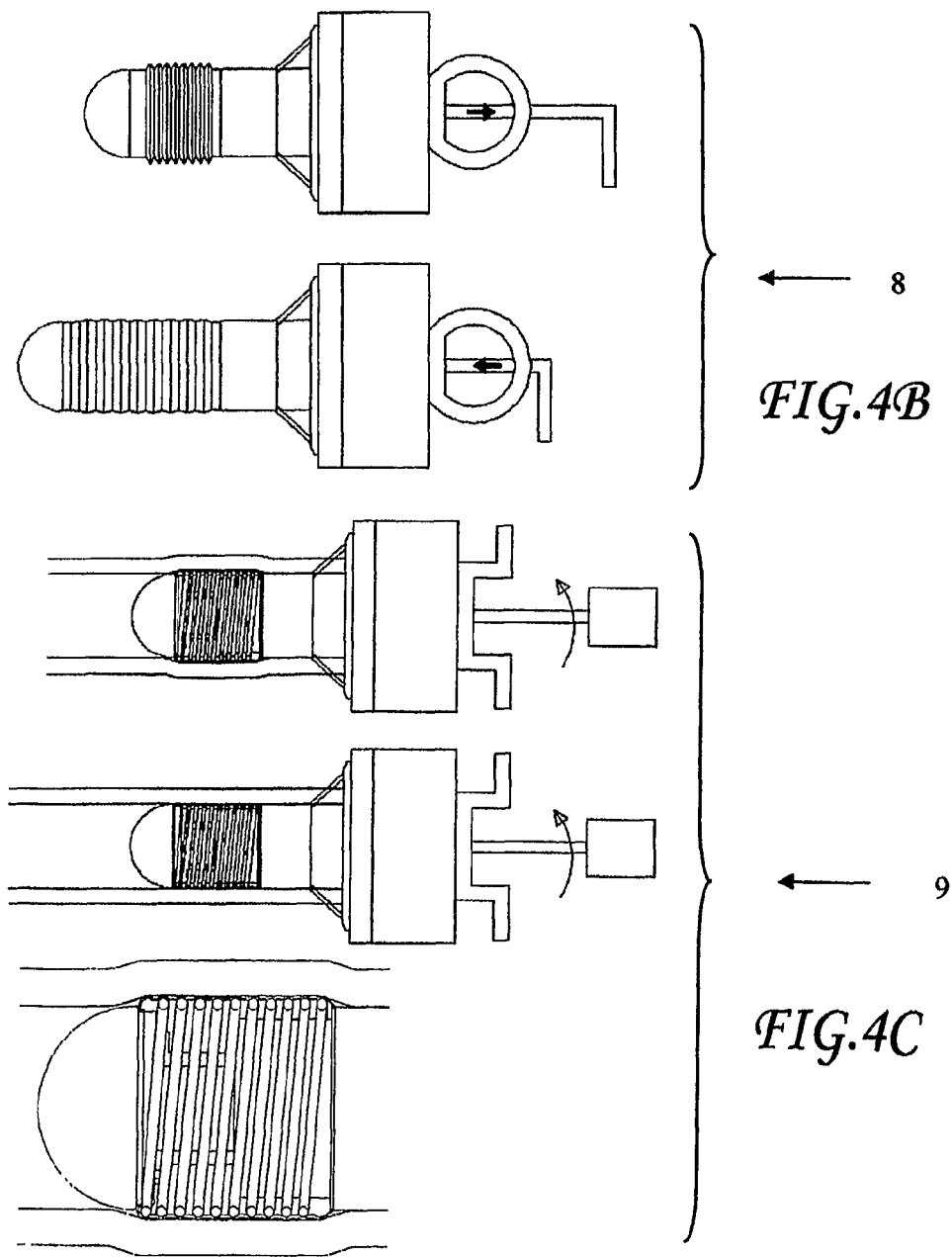
FIG.4B
FIG.4C

A

B  16     15     17

18

C

ASSISTED APPARATUS FOR ANASTOMOSIS AND METHOD THEREBY OF RECONNECTING THE URETHRA TO THE BLADDER AFTER REMOVAL OF THE PROSTATE DURING A PROSTATECTOMY

CROSS-REFERENCE TO RELATED APPLICATIONS

This application is a national stage of PCT/IL06/00595, filed May 21, 2006, which claims priority to Provisional Application No. 60/682,373, filed May 19, 2005.

FIELD OF THE INVENTION

The present invention relates to the reconnection of the urethra and bladder after removal of the prostate during a prostatectomy. Specifically, the invention relates to a method and an either automatic or semi-automatic device for performing a urethral-vesicle anastomosis. The invention is also intended for general use in tubular anastomosis.

BACKGROUND OF THE INVENTION

The prostate remains the second most common cause of cancer death. Because the incidence of prostate cancer increases more rapidly with age than does any other cancer and because the life expectancy is increasing, the number of men with prostate cancer and the number of deaths from the disease are expected to rise. Most prostate cancers detected nowadays are clinically localized and likely to be cured. A major treatment alternative for these patients includes radical prostatectomy, which is the complete surgical removal of the prostate gland along with its fascial coverings, requiring disconnecting the prostate from the urethra at the urogenital diaphragm and the urinary bladder at the bladder neck. To restore continuity of the urinary tract where the prostate has been removed, a new connection (anastomosis) of the bladder neck to the urethra must be accomplished. It is the attachment of the urethral stump to the bladder neck which is particularly difficult. This difficulty arises from several aspects including the tendency of the urethral stump to retract into adjacent tissue as well as its delicate structure mandating placement of thin and accurate sutures to ascertain that sufficient urethral tissue is incorporated into the anastomosis without damaging the sphincteric mechanism. Further complicating this procedure is the fact that the urethral stump is located beneath the pubic bone thus requiring that the surgeon work at a difficult angle and in positions that are uncomfortable and limiting.

A major impediment of radical prostatectomy remains its postoperative sequel related to the urethro-vesical anastomosis, which if not properly performed can lead to both urinary incontinence and outflow obstruction secondary to stricture at the anastomosis site.

Thus there remains a long felt need for the present invention relating to the reconnection of the urethra and bladder after a radical retropubic prostatectomy, specifically a method and device for performing a urethral-vesicle anastomosis.

SUMMARY OF THE INVENTION

A method and device are provided for the anastomosis of the urethra and bladder during radical retropubic prostatectomy. The surgeon inserts a guiding catheter into the urethra, which is attached in an end-to-end fashion to a semi-automatic bi-directional suture mechanisms inserted into the pelvis through the surgical wound. The catheter is then retracted outwardly to position the tip of the urethral suturing mechanism in the opening of the urethral stump. When the edge of the urethral suturing mechanism lies within the urethra, a mechanism is activated to position and hold the urethral stump in position to the suturing mechanism. One of the embodiments makes use of several protruding non-traumatic rounded flanges which secure the proximal edge of the urethra while causing protuberance and elongation of the urethral stump towards the pelvis, in another option following positioning vacuum is utilized to hold the urethral stump in position, other options are considered in the detailed description. In another aspect of this invention, the protruding flanges are part of the guiding catheter or alternatively, a guiding rigid sound. Another alternative is using the suturing device while maintaining the posterior urethral wall intact (i.e. cutting through the anterior wall only); the latter prevents the urethral stump from retracting towards the pubis and precludes the need to use the aforementioned protruding mechanism. Once the urethral stump has been adequately extended towards the pelvis, the suturing mechanism is activated driving a set of one or more needles and sutures from inside the urethral lumen outward towards an engagement ring, which is used to fixate the anchor/sutures following their complete deployment outside the urethra. Each needle retracts a corresponding suture (with or without an anchor) which travels from within the lumen of the urethra in an inside-outside fashion. Following threading the sutures the needles retract to their initial position. The suture driving mechanism comprises a piston that may move in a rotational or linear movement, and in addition may either be divided in a piston anchor fashion or as one unit that threads the suture through the urethral stump tissue. Following driving and positioning of the sutures (with or without an anchor) the needles/pistons retract to their initial position. The bladder suturing mechanism is then manoeuvred into the refashioned bladder neck. Subsequently, the surgeon activates a reciprocal mechanism which expels a set of needles (one or more) from within the bladder in an inside-outside fashion, driving the sutures in to a corresponding ring in the same fashion as in the previous urethral stump suturing mechanism. The device incorporates two suturing mechanism, one for the urethral stump and the other for the bladder neck. Preferably six sutures are attached by the mentioned suturing mechanism. Each of the mentioned suturing mechanisms threads one end of each of the sutures coupling the urethral stump to the bladder neck. Once the sutures have been incorporated into the urethral stump and the bladder neck, the urethral guiding catheter is detached from the urethral stump suturing mechanism. Both suturing mechanisms are detached from their sutures engagement rings and disposed. A Foley catheter is then passed from the urethral opening through the engagement rings and captivated sutures, into the bladder. At this point, the sutures encircle the catheter in 360 degrees. Each of the engaging rings is then fractured (for example) at their midline into two pieces, each comprising (as in this example) a set of three needles. The two parts are placed on the right and left side of the wound, correspondingly. The sutures are then manually tied by the surgeon, thus re-attaching the bladder to the urethral stump over the Foley catheter.

BRIEF DESCRIPTION OF THE FIGURES

The objects and advantages of various embodiments of the invention will become apparent from the following description when read in conjunction with the accompanying drawings wherein FIG. 1 schematically presents the anastomosis apparatus fully assembled according to one embodiment of the present invention;

FIGS. 4A and 4B and 4C schematically present alternative positioning mechanisms according to other embodiments of the present invention;

DETAILED DESCRIPTION OF THE EMBODIMENTS

Figure 1:
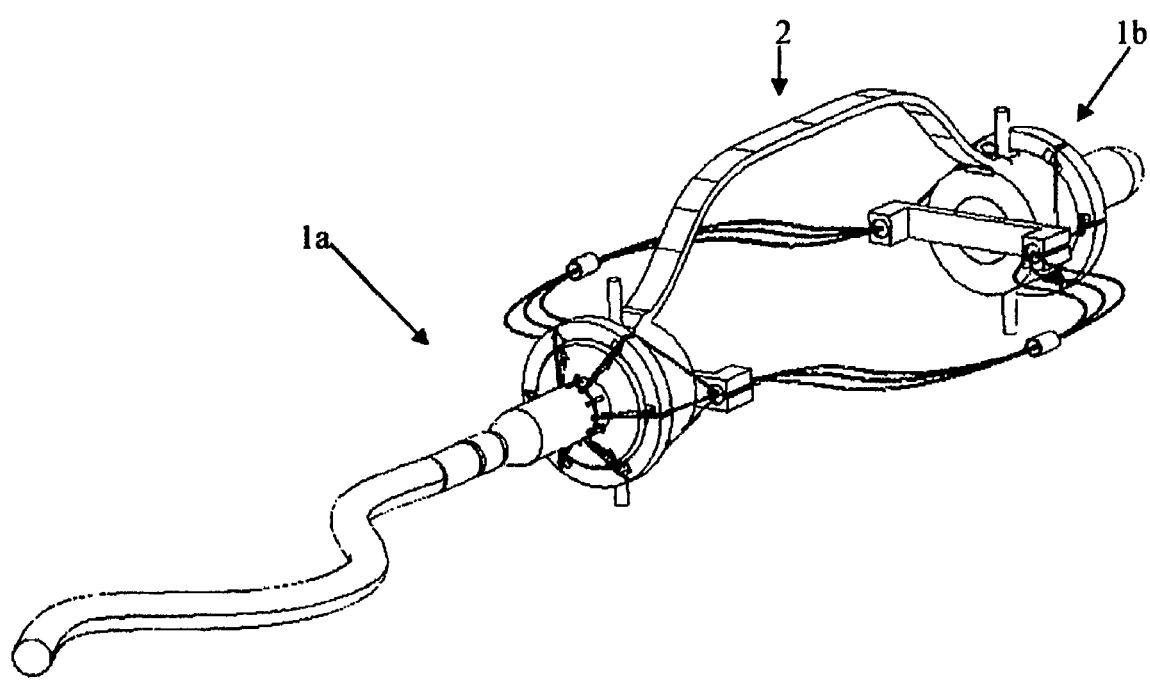

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide an apparatus for reconnecting the urethral stump to the neck of the bladder after removal of the prostate during a prostatectomy and method of performing urethral-vesicle anastomosis thereby.

The term piercing refers hereinafter in a non limiting manner to a needle deployment motion through body tissue walls.

It is according to one embodiment of the present invention to teach a method of performing a urethral-vesicle anastomosis inter alia comprising steps being defined below: A guiding catheter or sound is introduced into the urethra from the penis until it protrudes from the urethral stump. The guiding catheter is connected to the suturing device at the end of the urethral suture unit and retracted, thereby introducing the urethral suturing unit into the urethral stump. According to one embodiment of the present invention, the anastomosis is performed following complete removal of the prostate. In this embodiment, a mechanism is used to enable protrusion of the urethral stump towards the bladder, i.e. after it had retracted towards the penis, to facilitate adequate suture placement through the urethral stump. This mechanism can be an integral part of the suture unit but can also be situated in the guiding catheter. With the urethral stump bulging out, the needle deployment mechanism is activated, e.g., from within the suture unit, enabling piercing of the urethral wall in a radial or tangential fashion, preferably by 1 to 12, more specifically 6 needles. For sake of convenience, an example of 6 needles simultaneously utilized, penetrating through the body tissue wall at equidistant locations hereinafter follows.

Alternatively, and yet according to another embodiment of the present invention, the deployment of sutures through the urethral stump is performed before complete removal of the prostate. In this embodiment, the prostato-urethral junction is partially transacted, leaving at least a portion of the posterior urethral wall intact, e.g. from the 5 to 7 o'clock position. Consequently, active protrusion of the urethral stump as described above may be avoided.

The "needles" in the suture driving mechanism comprise a rotational or linear piston movement, and in addition may either be divided in a piston-anchor fashion, or as one unit that threads the suture through the urethral stump tissue, into the sutures engagement ring, with or without an anchor Any other number of needles or needle sets is similarly optional. Each needle threads a suture with or without an anchor, through the urethral wall from the inside, in one of the options and is anchored in the anchoring/engagement ring about the urethral stump. The positioning mechanism may now be contracted and the suture unit may be removed from the urethral stump. The bladder neck suturing mechanism is attached to the urethral stump suturing unit by means of a flexible crossbar and the sutures leading from the inside of the urethral stump continue to the second suture unit where they are attached to the "needles" of its piercing device. The bladder neck suturing unit is inserted into the bladder's neck, and a similar positioning and threading procedure is preformed the bladder neck suturing mechanism is used to pass the needles and sutures through the wall of the bladder neck.

Each needle pulls the suture leading from its equivalent position on the urethral stump through the wall of the bladder neck.

The needle in one embodiment or the suture in another embodiment becomes anchored in a second needle/suture-anchoring ring. The bladder neck positioning mechanism is now contracted and the suture unit is removed from the bladder. The two suture units and the crossbar are detached from the needle/suture-anchoring rings and retracted through the wound. A Foley catheter is now passed through the urethra and into the bladder. Each of the anchoring rings is now divided into two (optional 2) semicircular sections and retracted through the wound. A balloon at the end of the Foley catheter now situated within the bladder is now inflated, and by pulling the catheter outwardly from the penis the urethra stump and the bladder neck make contact, simultaneously the sutures are drawn tight and the surgeon ties the sutures manually and thereby completes a urethral-vesicle anastomosis.

The term 'urethral stump' is related hereinafter to the distal portion of the urethra remaining after the prostate has been removed.

The term 'bladder neck' or 'neck of the bladder' is related hereinafter to the proximal portion of the urethra remaining after the prostate has been removed, alternatively to the opening to the bladder.

The term 'plurality' applies hereinafter to any integer greater than or equal to one.

The terms 'needle' or 'needles' apply hereinafter to a plurality of needles, harpoons or any other threading means It is acknowledged in this respect that the physician may determine the number and the location of needled being operated in each set of needle insertion. For example, whereat the total number of needles utilized in this semi-automatic operation is six, three sets of two needles or two sets of three needles can be used.

It is according to another embodiment of the present invention to disclose an anastomosis apparatus for the reconnecting the urethral stump to the neck of the bladder after removal of the prostate during a prostatectomy. The apparatus comprises two suture units at least a section of one has suitable dimensions to be introduced into the bladder neck and at least a section of the other has dimensions suitable to be introduced into the urethral stump. Each suture unit comprises a positioning mechanism which tightens the surrounding tissue and prepares it for threading, a threading device which passes about six needles, harpoons or any other threading means through the surrounding tissue, each needle drawing a suture through the tissue and a needle/suture-anchoring ring into which the needles/sutures become embedded after passing through the surrounding tissue. The urethral suture device additionally comprises a connecting means by which it is attached to a guiding catheter or sound protruding from the urethral stump.

It is according to a further embodiment of the present invention to disclose an anastomosis apparatus for the reconnecting the urethral stump to the neck of the bladder wherein the positioning mechanism comprises six plungers each comprising a shaft and a member lying parallel to the shaft and pivoted to it in such a manner that sliding the plunger in a groove along the length of the suture unit causes the pivoted member to rotate into an orientation orthogonal to the length of the shaft. The combined effect of six plungers being activated inside the urethral stump or the bladder neck is that the effective diameter of the suture unit thereby positioning the surrounding tissue.

It is according to another embodiment of the present invention to disclose an anastomosis apparatus for the reconnecting the urethral stump to the neck of the bladder wherein the positioning mechanism comprises a spring, concertina or other mechanism in which the diameter is increased by shortening the length of the device.

Another embodiment of the present invention discloses an anastomosis apparatus for the reconnecting the urethral stump to the neck of the bladder wherein the positioning mechanism comprises at least one inflatable member the volume of which can be increased when introduced into the urethra or the bladder neck.

It is according to a further embodiment of the present invention to disclose an automatic or semi-automatic anastomosis apparatus for the reconnecting the urethral stump to the neck of the bladder wherein the threading unit comprises at least six plungers each connected to a needle by a connector lying in a groove along the length of the suture unit. With the suture unit inside the urethra or bladder neck, a mechanism is used to slide the plungers along the groove forcing the needles to pierce the surrounding tissue, drawing/threading the sutures through the wall/tissue.

It is according to another embodiment of the present invention to disclose an anastomosis apparatus for the reconnecting the urethral stump to the neck of the bladder wherein the threading unit comprises at least six harpoons. Each harpoon is mounted upon a semicircular piercing shaft which is connected to a gear wheel which interlocks with a toothed shaft. With the suture unit inside the urethral stump or bladder neck, a mechanism is used to push the toothed shaft thereby rotating the gear wheel which forces the harpoon to pierce the surrounding tissue, drawing and threading the sutures through the wall/tissue.

It is according to yet another embodiment of the present invention to disclose an anastomosis apparatus for the reconnecting the urethral stump to the neck of the bladder wherein the harpoon piercing/threading unit is orientated such that the harpoons are directed into the urethral stump from the outside to become embedded in the suture unit within the urethral stump.

A further embodiment of the present invention discloses an anastomosis apparatus for the reconnecting the urethral stump to the neck of the bladder wherein the suture device additionally comprises a smooth outer sheathing which covers the piercing device and the distending device and is of a shape and texture suitable for the smooth introduction into the urethral stump or the bladder neck.

Another embodiment of the present invention discloses an anastomosis apparatus for the reconnecting the urethral stump to the neck of the bladder wherein the urethral suture device additionally comprises a means by which it is connected to a guiding catheter, comprising a screw thread, a smart connector for fast connection or any other connecting means.

Another embodiment of the present invention discloses an anastomosis apparatus for the reconnecting the urethral stump to the neck of the bladder wherein the needle-anchoring rings each comprise silicon rings, although it is recognised that other materials may be used, the inner diameter of the ring is suitable for the ring to be mounted about the suture unit. The outer circumference of the ring is characterised by at least six equidistant guiding notches which are used to hold the sutures in position. Once the needles have pierced the wall of the urethral stump or bladder neck they enter the ring and are locked into place. Possible locking means include the needles becoming embedded in some adhesive material such as wax, silicon, cork, rubber, two rings being twisted so as to lock the needle into place between them, clasping means being fastened together, grooved needles becoming hooked onto a ratchet like structure or any other locking means.

It is according to a further embodiment of the present invention to disclose an anastomosis apparatus for the reconnecting the urethral stump to the neck of the bladder wherein the needle-anchoring rings each comprise two semicircular sections which are separated during the last stages of the operation such that the rings can be removed and reused.

It is according to a further embodiment of the present invention to disclose an anastomosis apparatus for the reconnecting the urethral stump to the neck of the bladder wherein The needles are positioned in the one o'clock, three o'clock, the five o'clock, seven o'clock, nine o'clock and eleven o'clock positions, although it is acknowledged that other arrangements are possible, particularly the addition of a needle at the six o'clock position.

It is according to a further embodiment of the present invention to disclose an anastomosis apparatus for the reconnecting the urethral stump to the neck of the bladder wherein at least six sutures are each connected to a needle in one suture unit and pass through a guiding notch in the outer circumference of a needle-anchoring ring. The three sutures from the one, three and five o'clock positions pass through a holding ring on one side of the anastomosis apparatus, the three sutures from the seven, nine and eleven o'clock positions pass through a holding ring on the other side of the anastomosis apparatus. Each suture then passes through the guiding notch in the equivalent position on the second needle-anchoring ring and is connected to the needle in the equivalent position of the second suture unit.

It is still according to a last embodiment of the present invention to disclose anastomosis apparatus for the reconnecting the urethral stump to the neck of the bladder wherein the sutures are individually colored so that each is easily distinguished from the others.

It is according to a last embodiment of the present invention to disclose a tubular anastomosis apparatus for the reconnecting of any tubular structures in the body such as the esophagus, trachea, blood vessels or sections of the gastrointestinal tract, particularly after the removal of a section.

Reference is made now to FIG. 1 schematically presenting a fully assembled anastomosis apparatus according to one embodiment of the invention. The apparatus comprises two suture units, 1*a* and 1*b*, a section of one has suitable dimensions to be introduced into the bladder neck, 1*b*, and at least a section of the other has dimensions suitable to be introduced into the urethral stump, 1*a*. The two are connected by a semi-flexible cross bar, 2.

Figure 2:
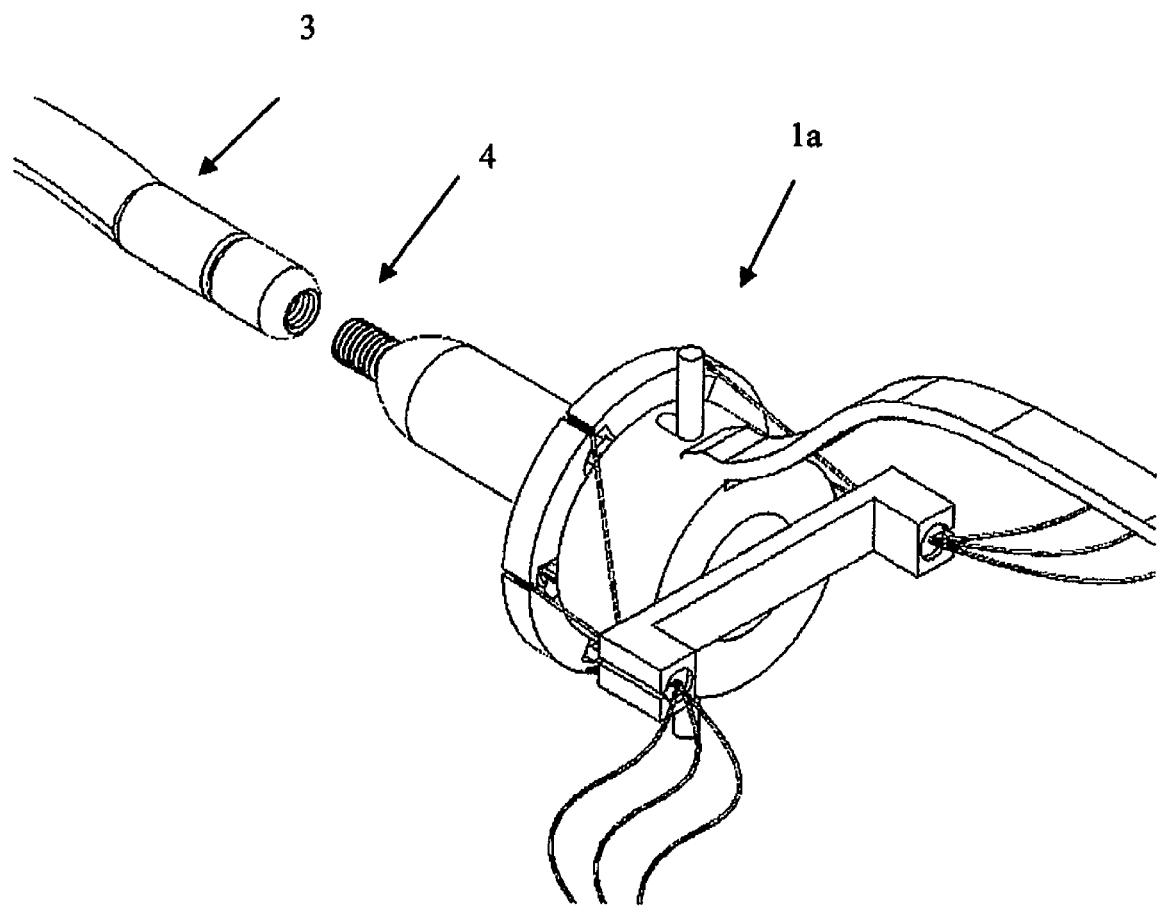
FIG. 2 schematically presents the urethral suture unit, the guiding catheter and one possible connecting means according to another embodiment of the present invention.

Reference is now made to FIG. 2 schematically presenting the urethral suture unit, 1*a*, the guiding catheter, 3, and one possible connecting means, 4, according to another embodiment of the present invention.

Figure 3A:
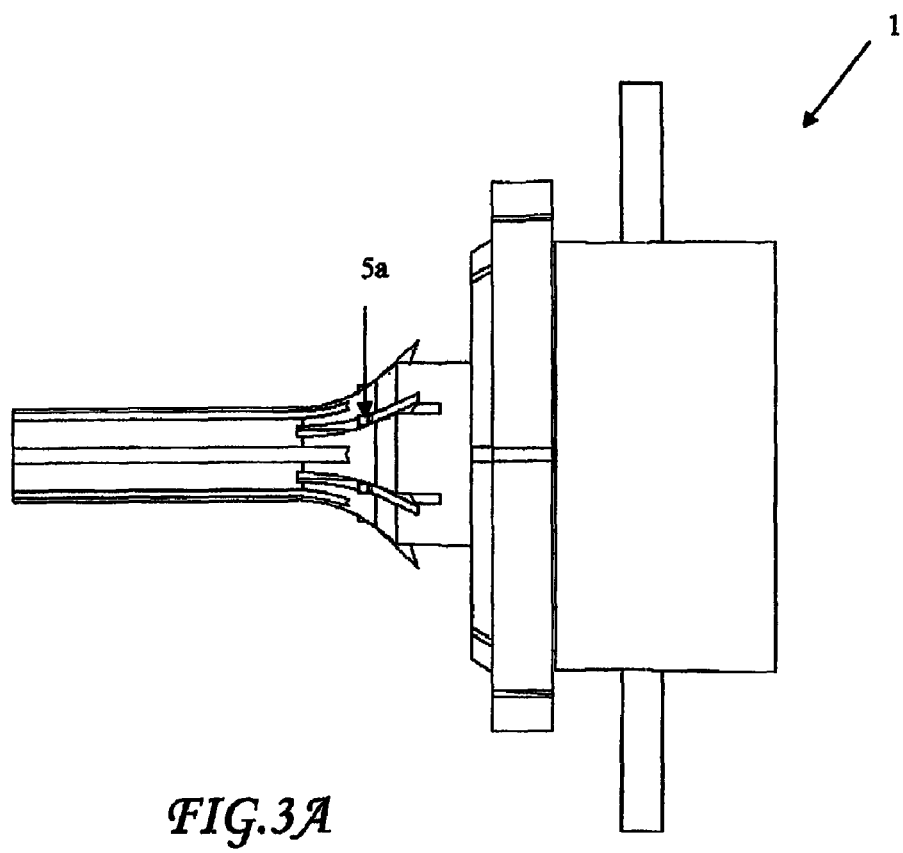
FIGS. 3A and 3B schematically present a side view of the suture unit with a possible positioning mechanism in both the distended and non-distended orientations according to another embodiment of the present invention.
Figure 3B:
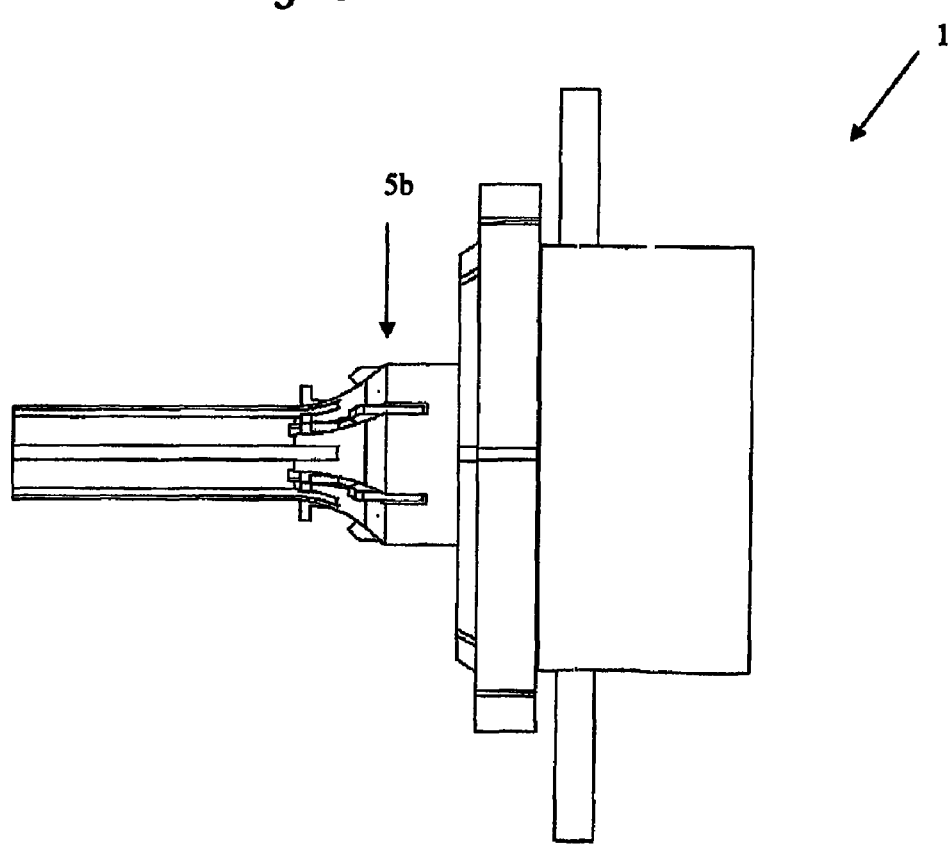

Reference is now made to FIGS. 3A and 3B schematically presenting the suture unit, 1, with a possible distending device in both the distended, 5*a*, and non-distended, 5*b*, orientations according to another embodiment of the present invention.

Reference is now made to FIGS. 4A, 4B and 4C schematically presenting alternative distending devices according to other embodiments of the present invention. The first (5) comprises six plungers each comprising a shaft, 6, and a member lying parallel to the shaft, 7, and pivoted to it in such a manner that sliding the plunger in a groove along the length of the suture unit causes the pivoted member to rotate into an orientation orthogonal to the length of the shaft. Alternatives shown include a concertina (8) and a spring (9) or other mechanism in which the diameter is increased by shortening the length of the device.

Figure 5:
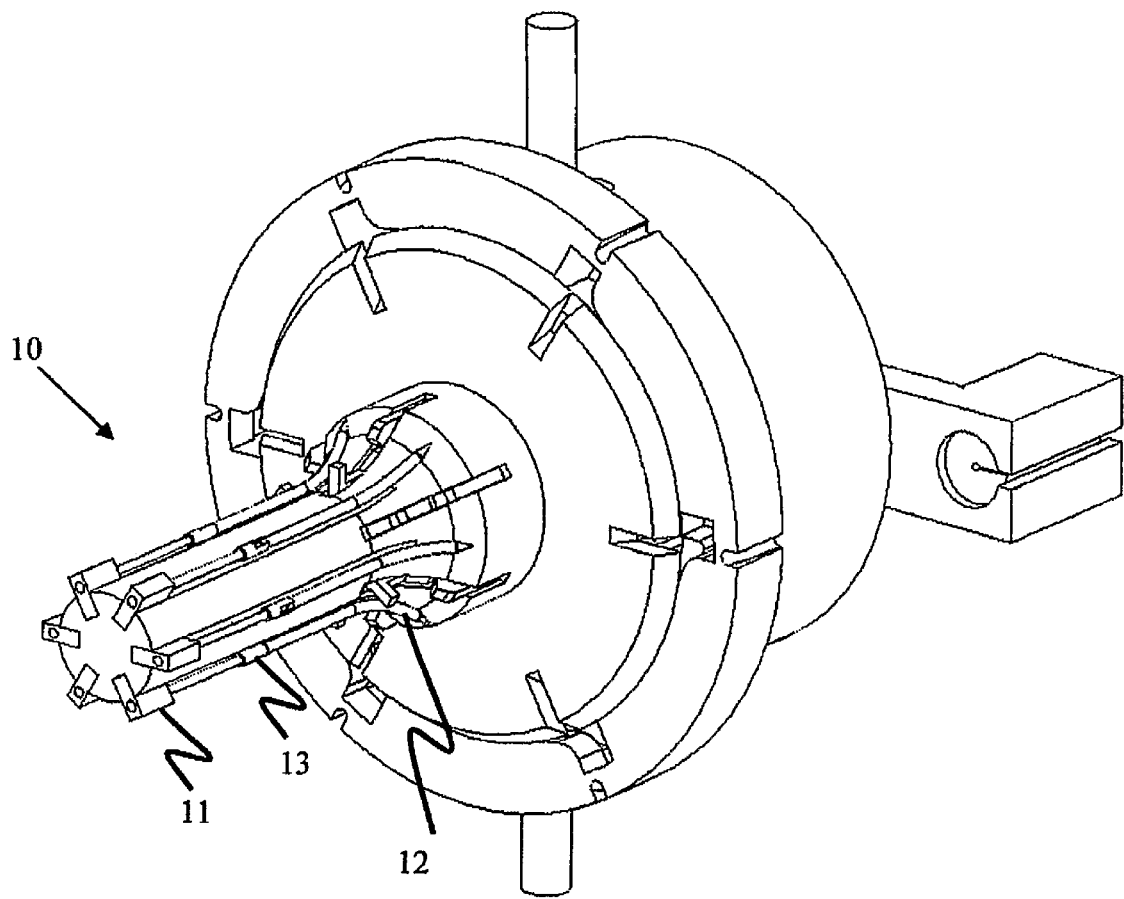
FIG. 5 schematically presents a suture unit with a plunger piercing unit before piercing according to another embodiment of the present invention.

Reference is now made to FIG. 5 schematically presenting a suture unit with a plunger piercing unit before piercing according to another embodiment of the present invention. The piercing unit, 10, comprises six plungers, 11, each connected to a needle, 12, by a connector, 13, lying in a groove along the length of the suture unit.

Figure 6:
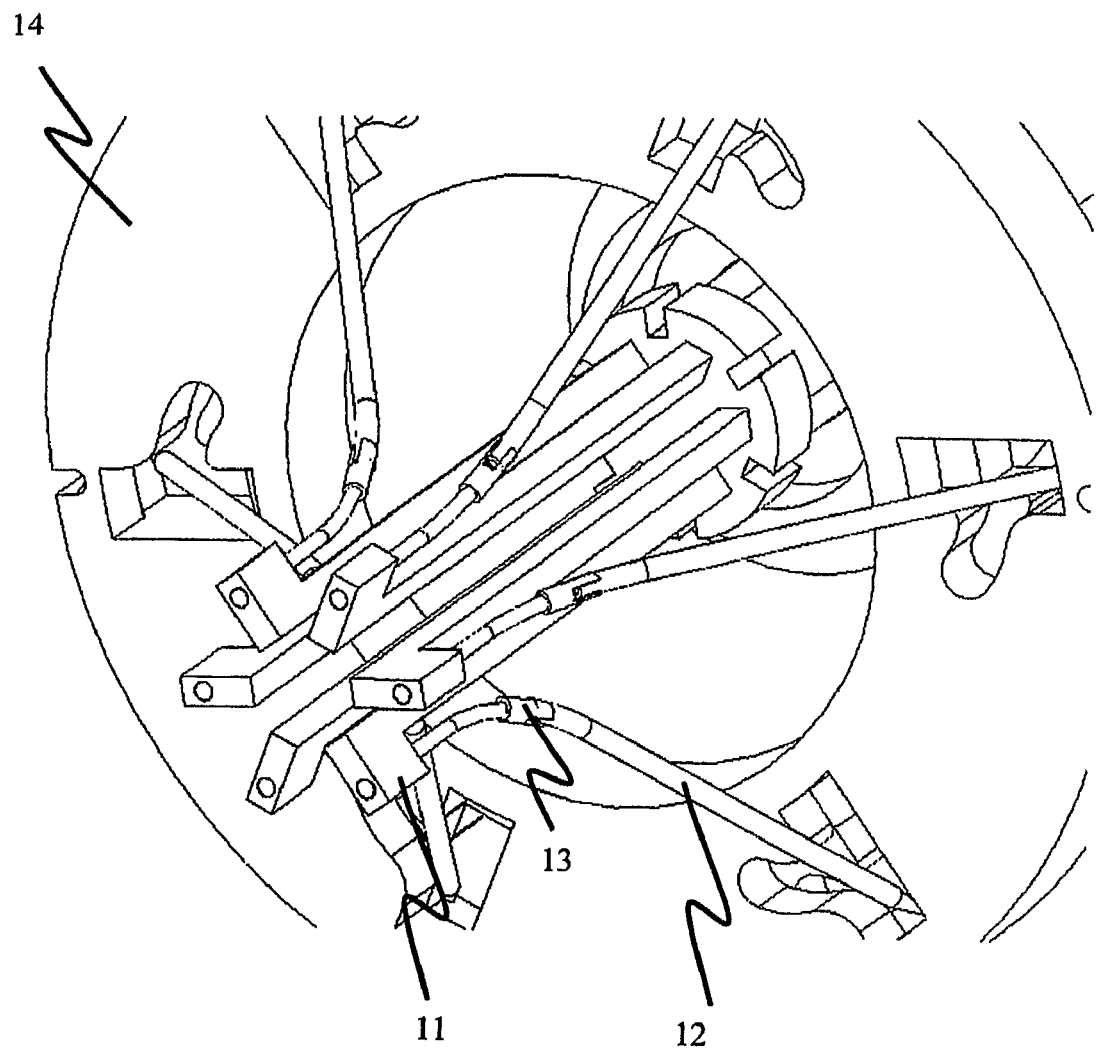
FIG. 6 schematically presents a suture unit with a plunger piercing unit after piercing according to another embodiment of the present invention.
Figure 7:
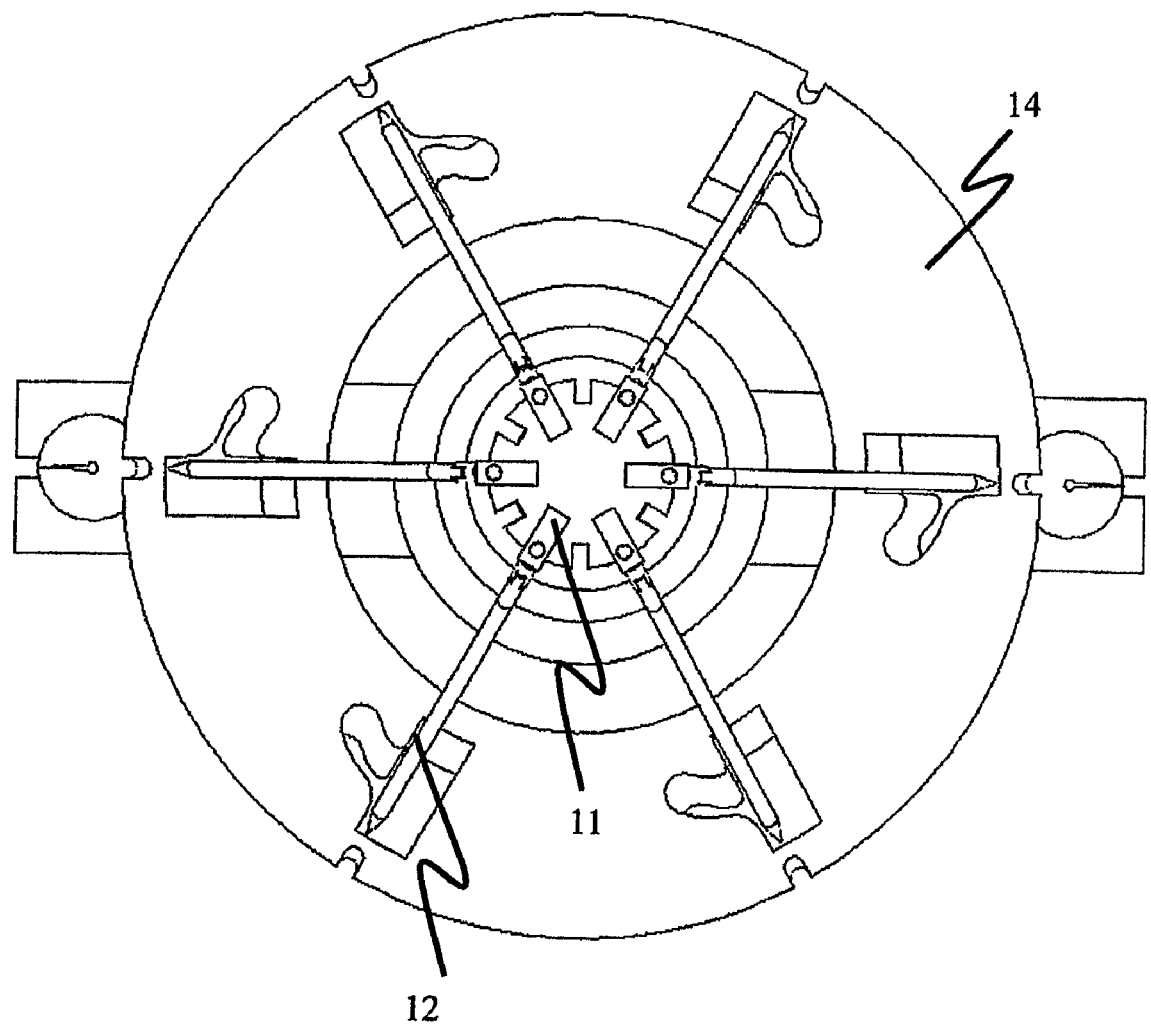
FIG. 7 schematically presents a plunger piercing unit with needles embedded in the needle-anchoring ring according to another embodiment of the present invention.

Reference is now made to FIGS. 6 and 7 schematically presenting a plunger piercing unit with needles embedded in the needle-anchoring ring, 14, according to another embodiment of the present invention.

Figure 8A:
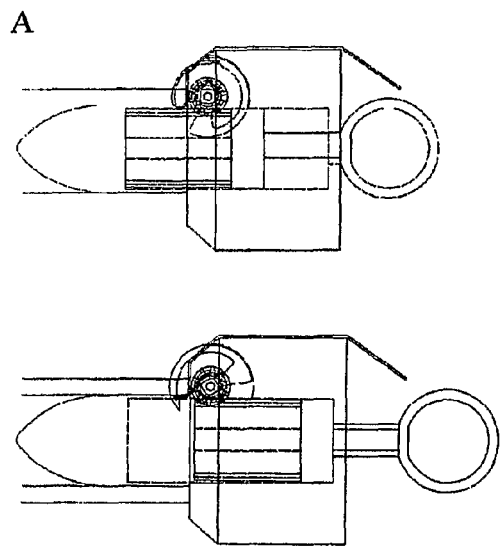
FIGS. 8A, 8B and 8C schematically present an anchor/harpoon piercing unit according to another embodiment of the present invention.
Figure 8B:
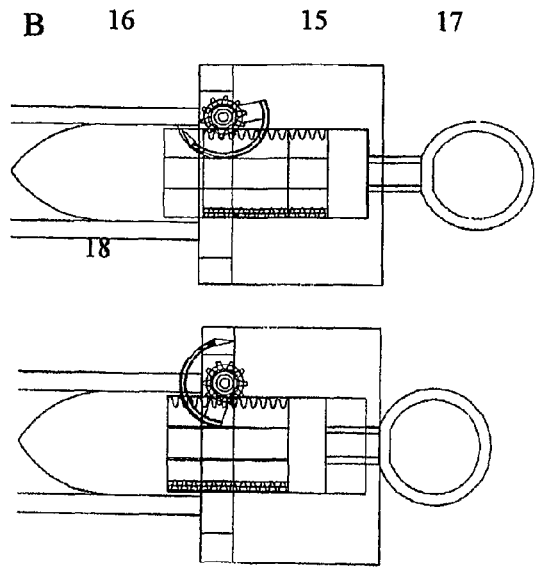
Figure 8C:
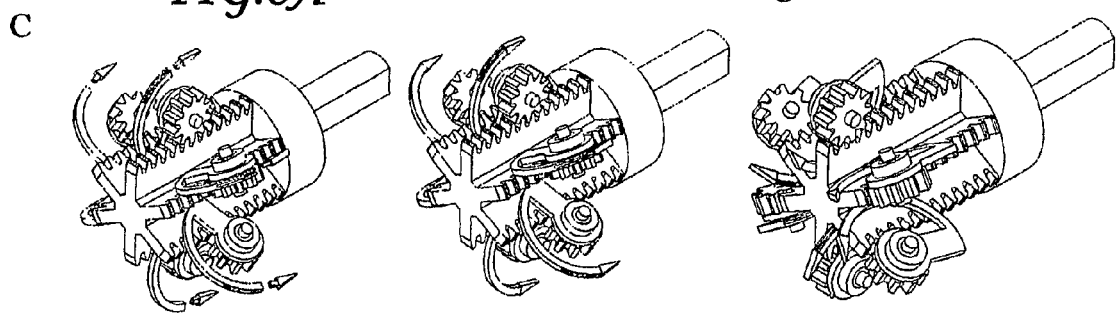

Reference is now made to FIGS. 8A, 8B and 8C schematically presenting a harpoon piercing unit after piercing according to another embodiment of the present invention. The device harpoon comprises at least six harpoons, 18. Each harpoon is mounted upon a semicircular piecing shaft, 15, which is connected to a gear wheel, 16, which interlocks with a toothed shaft, 17. With the suture unit inside the urethral stump or bladder neck, a mechanism is used to push the toothed shaft thereby rotating the gear wheel which forces the harpoon to pierce the surrounding tissue. Two alternative orientations are here represented. Figure set A represents the piercing unit in which the harpoons are directed into the urethral stump from the outside to become embedded within the suture unit. Figure set B represents the piercing unit in which the harpoons are directed out of the urethral stump to become embedded in the anchoring ring.

Figure 9:
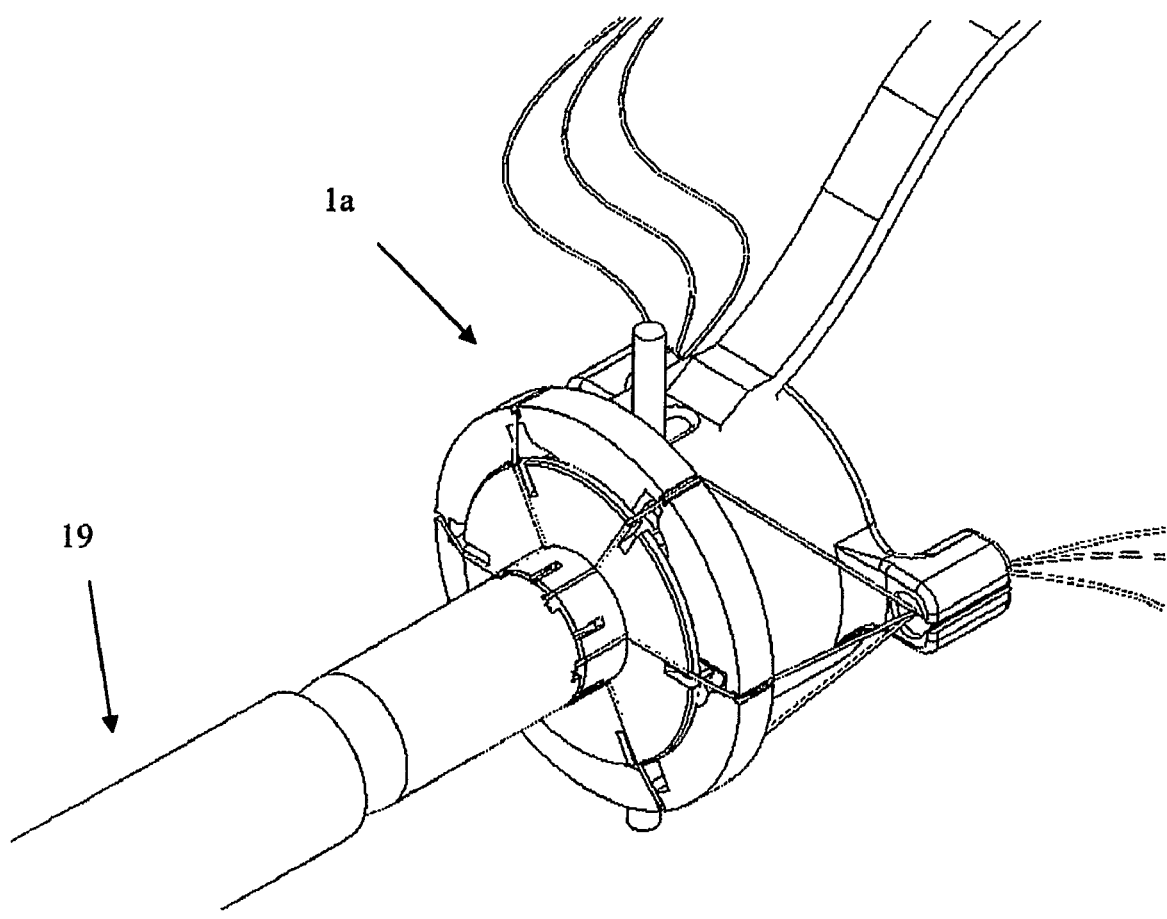
FIG. 9 schematically presents the urethral suture device introduced into the urethral stump according to another embodiment of the present invention.

Reference is now made to FIG. 9 schematically presenting a urethral suture device, 1*a*, introduced into the urethral stump, 19, according to another embodiment of the present invention.

Figure 10:
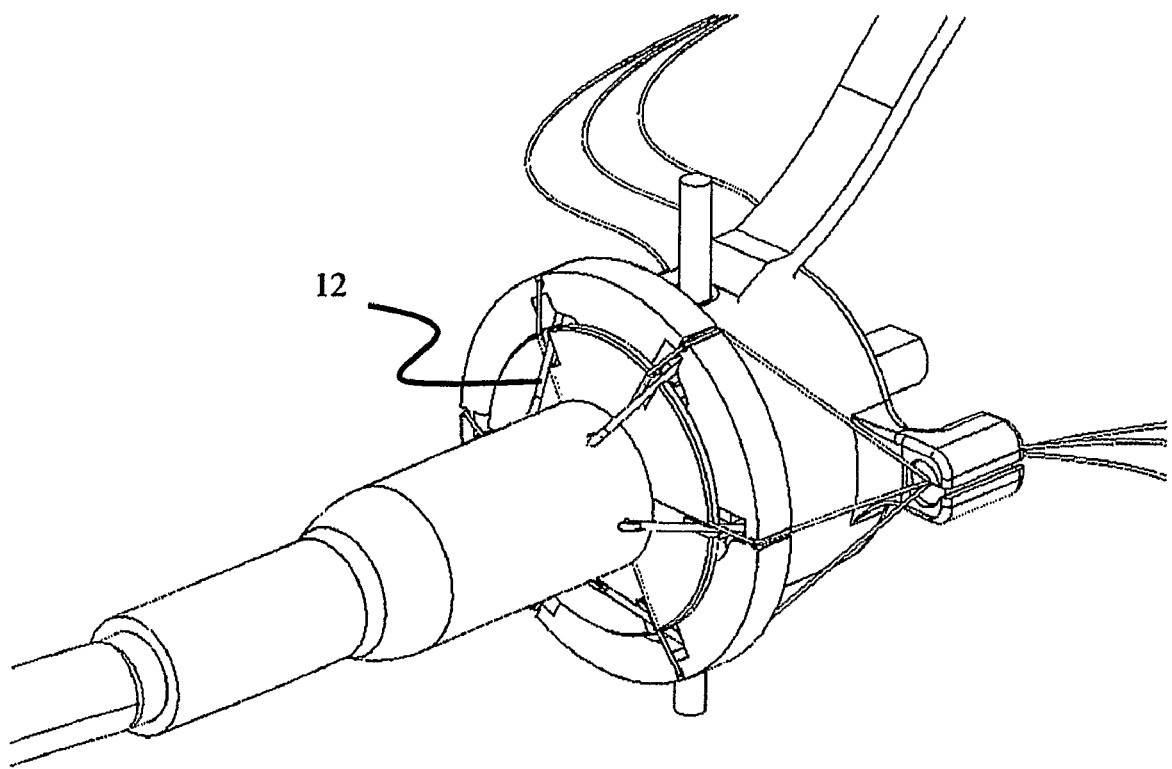
FIG. 10 schematically presents the urethral suture device piercing the walls of the urethral stump and the needles becoming embedded in the needle-anchoring ring according to another embodiment of the present invention.

Reference is now made to FIG. 10 schematically presenting a urethral suture device piercing the walls of the urethral stump and the needles, 12, becoming embedded in the needle-anchoring ring, 14, according to another embodiment of the present invention.

Figure 11:
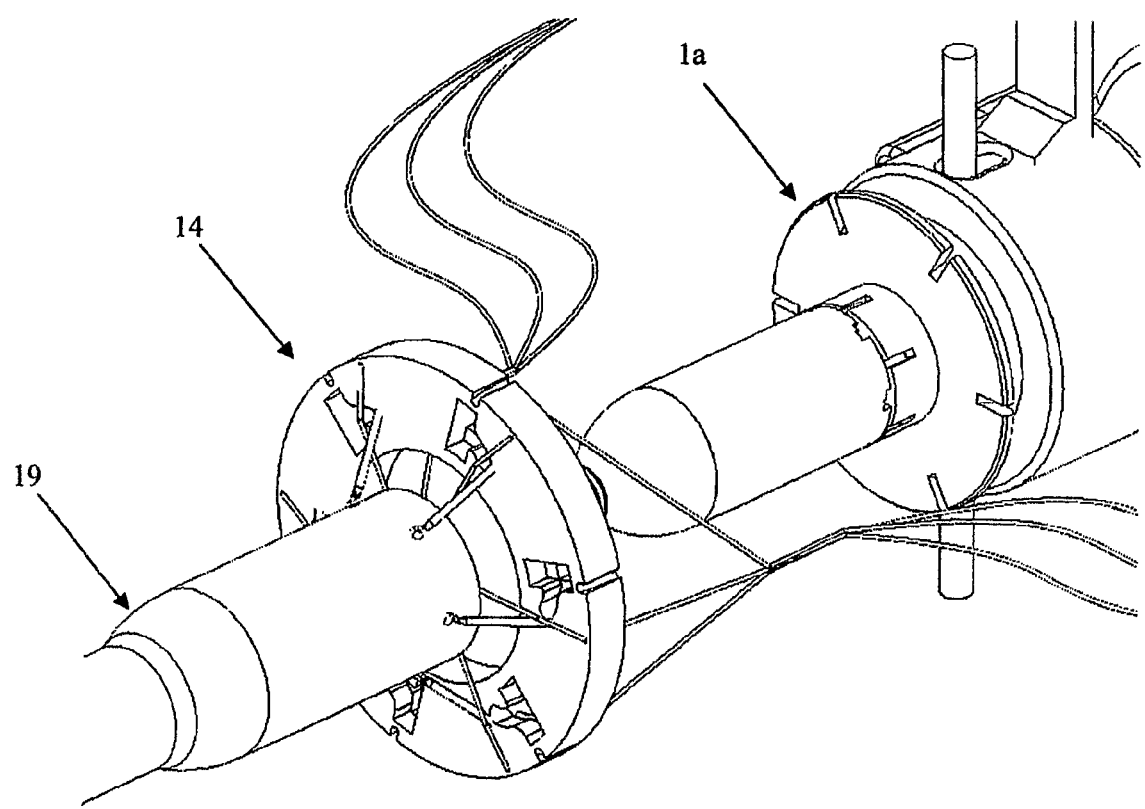
FIG. 11 schematically presents the urethral suture device being removed from the urethral stump, leaving in place the needle-anchoring ring according to another embodiment of the present invention.

Reference is now made to FIG. 11 schematically presenting a urethral suture device, 1*a*, being removed from the urethral stump, 19, leaving in place the needle-anchoring ring, 14, according to another embodiment of the present invention.

Figure 12:
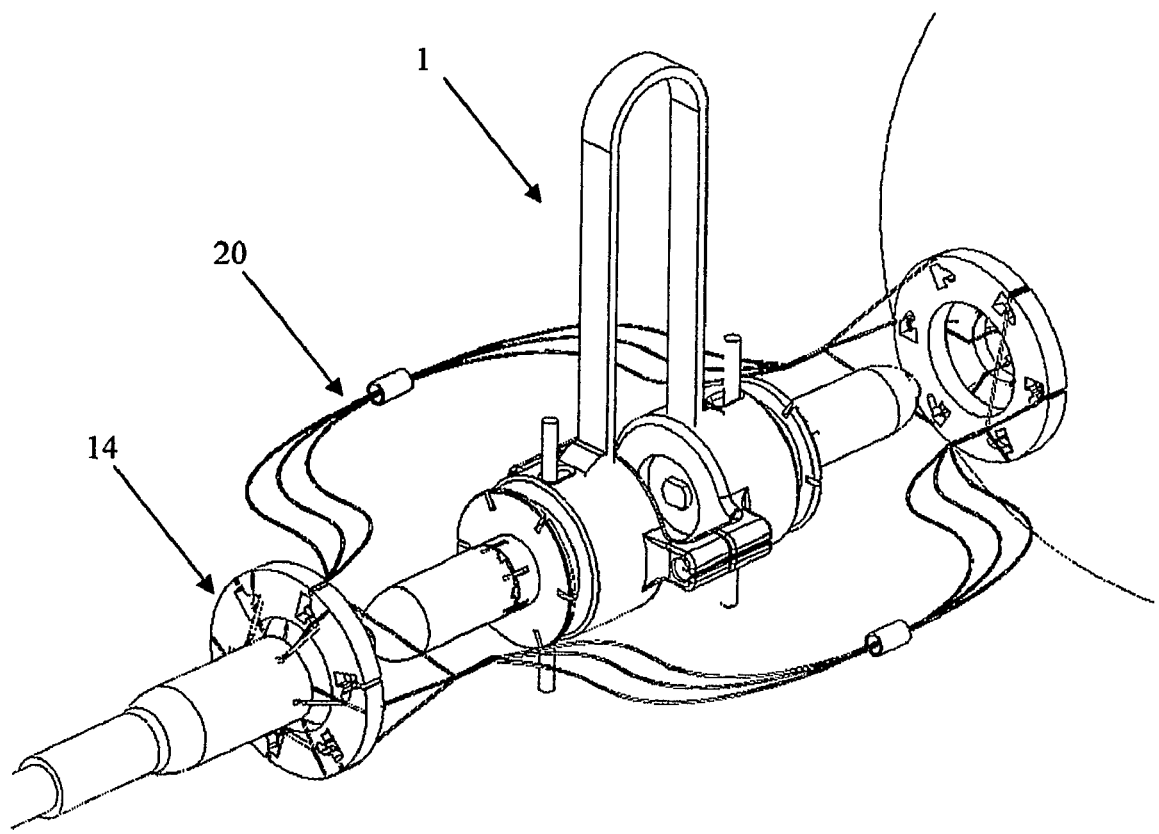
FIG. 12 schematically presents the suture units being withdrawn leaving the sutures and needle-anchoring rings in place according to another embodiment of the present invention.

Reference is now made to FIG. 12 schematically presenting the suture units, 1 comprising 1*a* and 1*b*, being withdrawn leaving the sutures, 20, and needle-anchoring rings, 14, in place according to another embodiment of the present invention.

Figure 13:
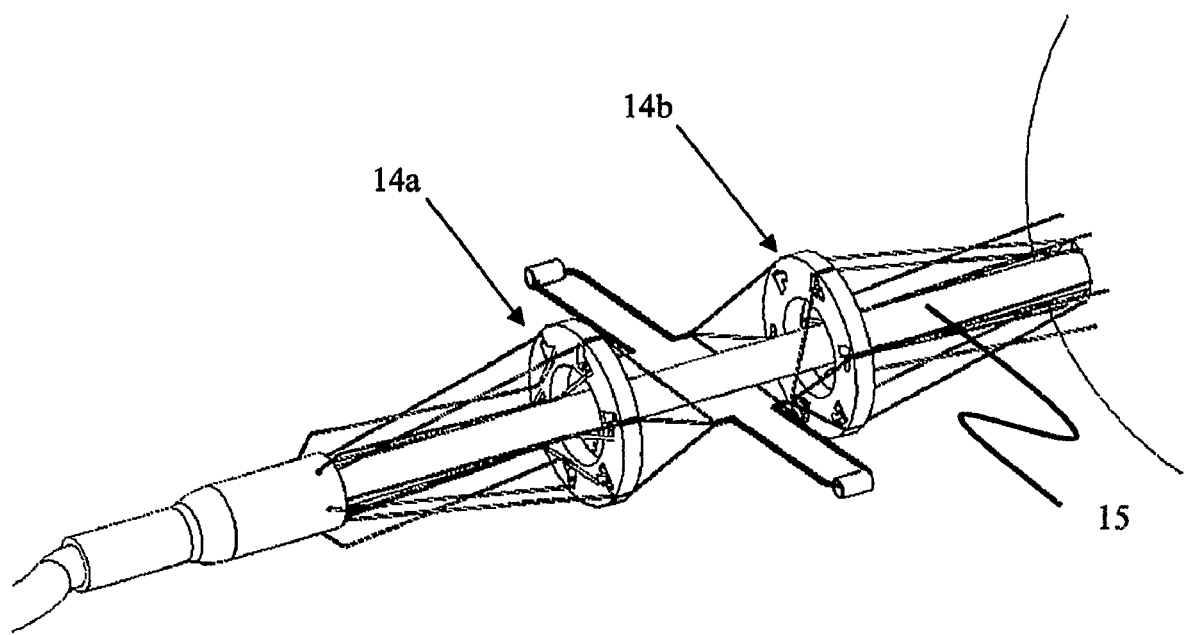
FIG. 13 schematically presents the needle-anchoring rings being drawn together over a Foley catheter according to another embodiment of the present invention.

Reference is now made to FIG. 13 schematically presenting the needle-anchoring rings, 14*a* and 14*b*, being drawn together over a Foley catheter, 15, according to another embodiment of the present invention.

Figure 14:
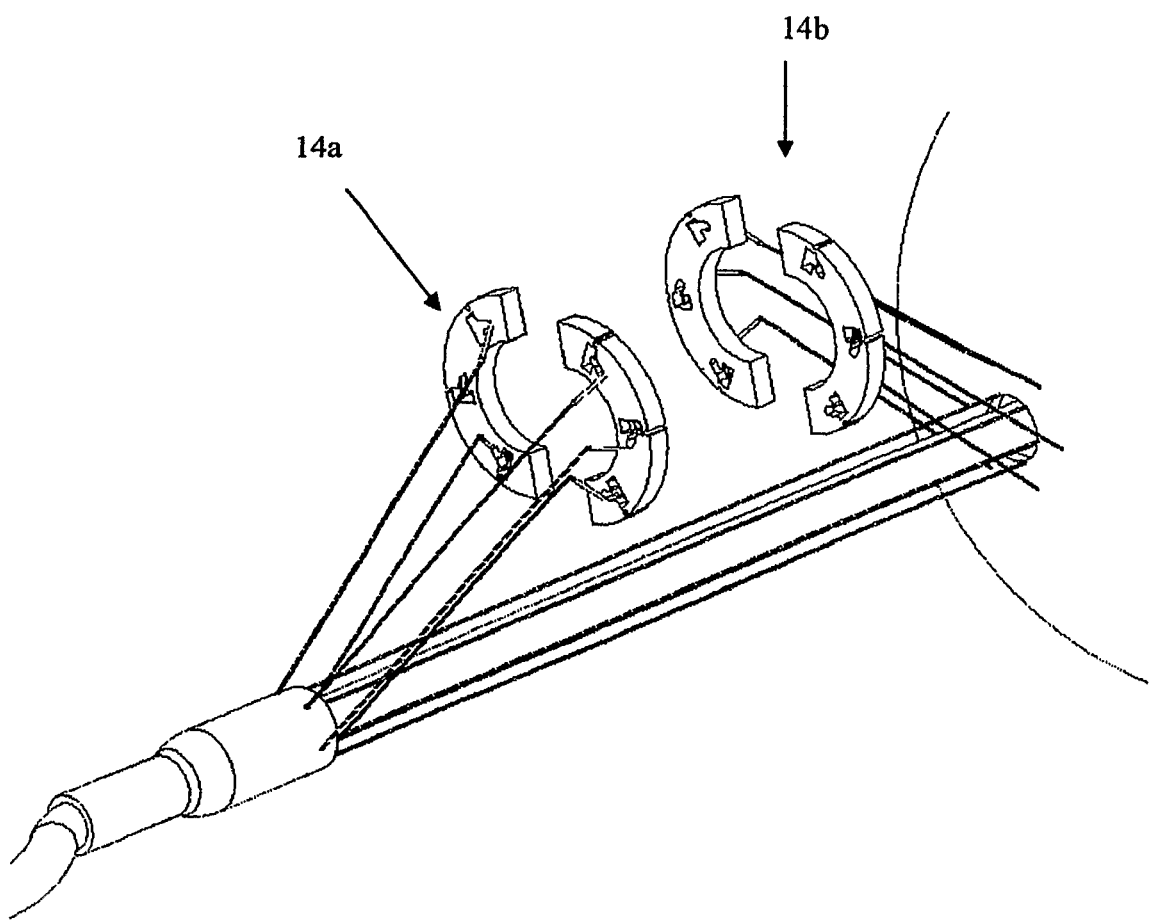
FIG. 14 schematically presents the needle-anchoring rings being fractured and withdrawn according to another embodiment of the present invention.

Reference is now made to FIG. 14 schematically presenting needle-anchoring rings, 14a and 14b, being fractured and withdrawn according to another embodiment of the present invention.

Figure 15:
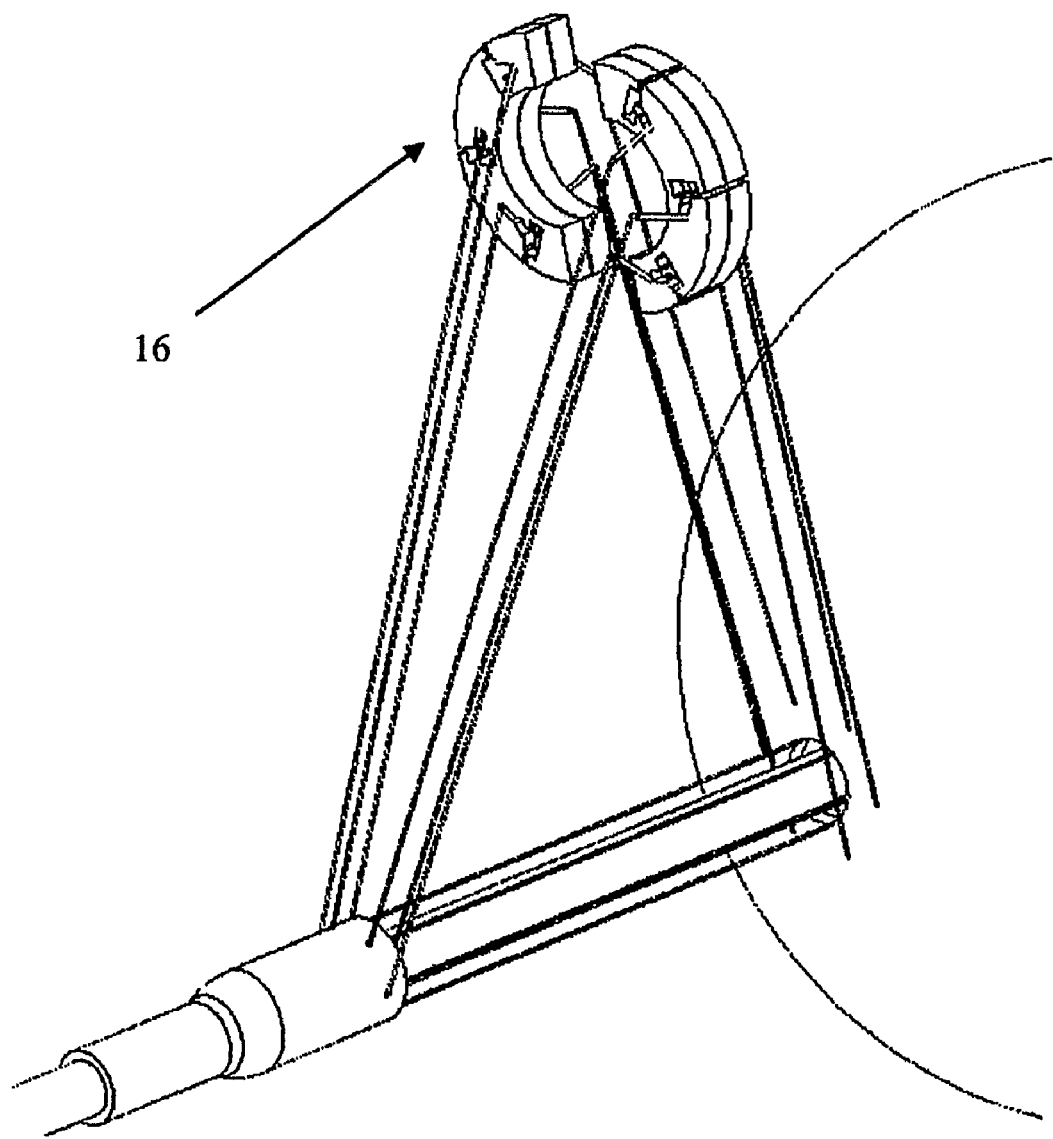
FIG. 15 schematically presents the fractured needle-anchoring semicircular sections being withdrawn in pairs according to another embodiment of the present invention.

Reference is now made to FIG. 15 schematically presenting the fractured needle-anchoring semicircular sections, 16, being withdrawn in pairs according to another embodiment of the present invention.

Figure 16:
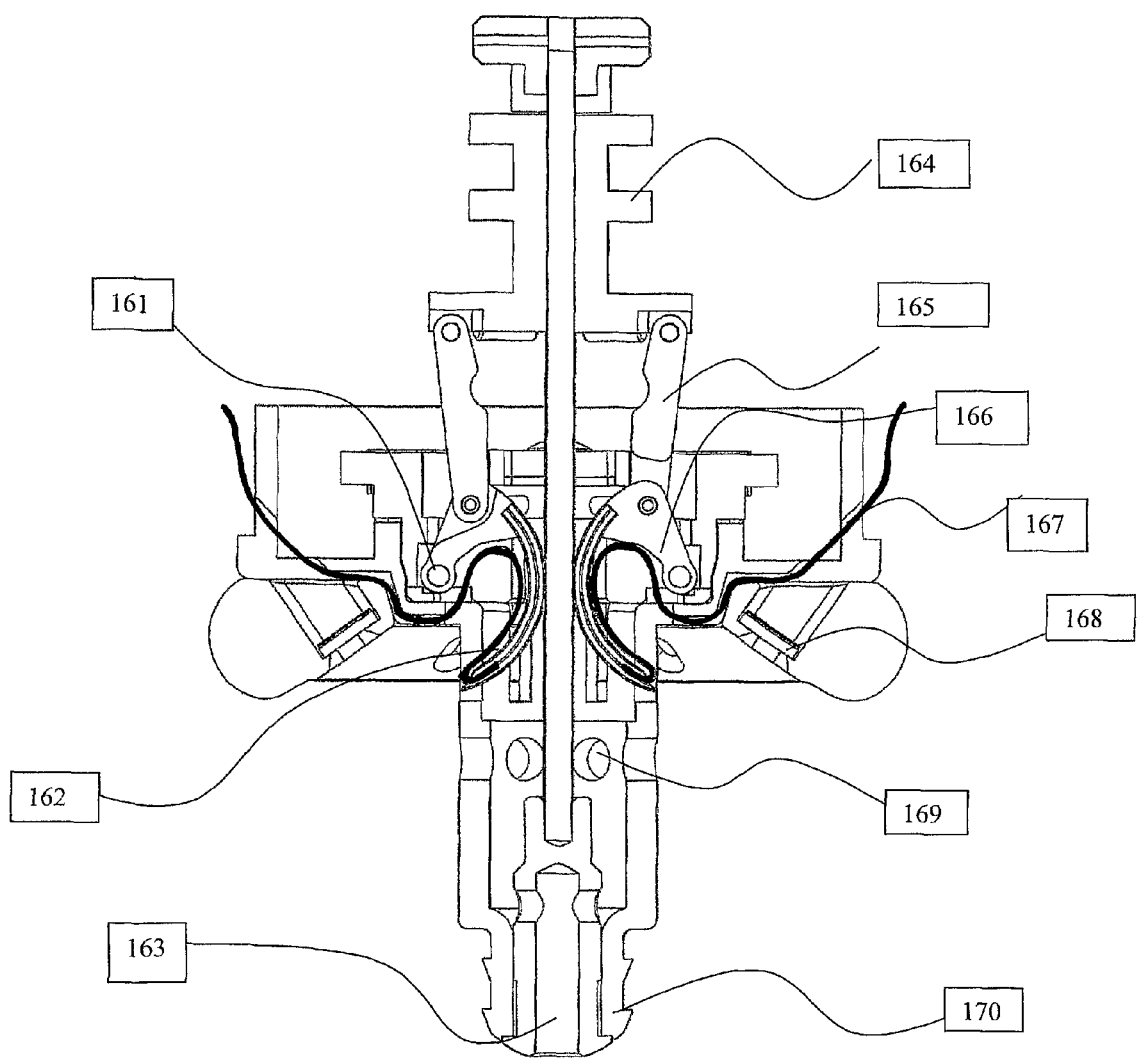
FIG. 16 schematically presents the urethral stump suturing device at the "start position" according to another embodiment of the present invention.

Reference is now made to FIG. 16 schematically presenting the urethral stump suturing device—at the "start position"—this mechanism is attached to a closely similar bladder neck suturing mechanism, as in the previous embodiment illustrated in FIG. 1 according to another embodiment of the present invention. The mechanism comprises six needle axis (161), six suture needles (162), air/fluid inlet/outlet—supply the positioning/holding holes (163), linear arm plunger (164), six push/pull arms (165), six suture needle rotating arms (166), six sutures (167), six suture capture mechanism (168), six suction/pressure holes for tissue positioning and holding (optional embodiment) (169) and a connector to the catheter (170).

Figure 17:
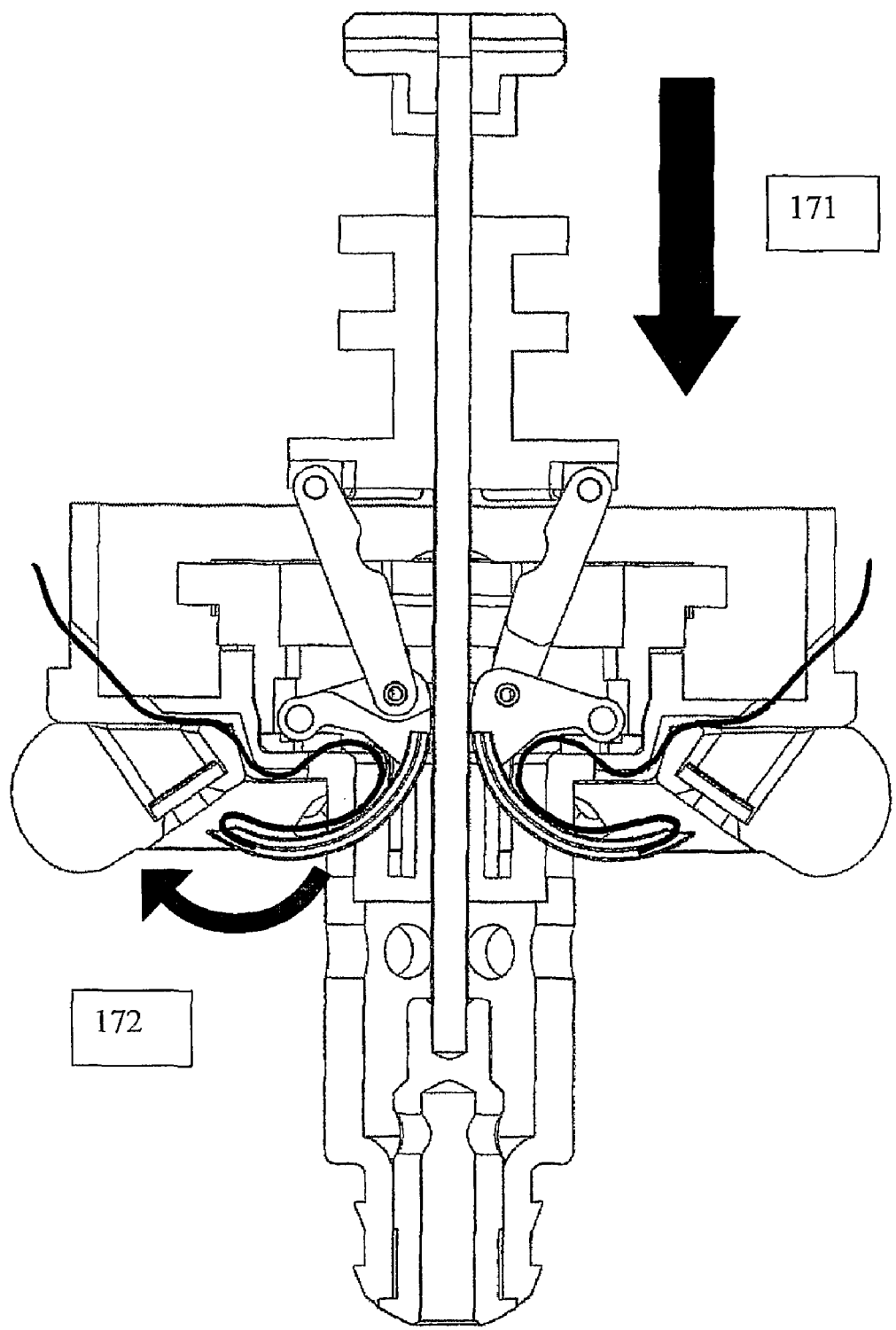
FIG. 17 schematically presents the urethral stump suturing device at mid position.

Reference is now made to FIG. 17 schematically presenting the urethral stump suturing device at mid position according to another embodiment of the present invention. The needles rotate with the sutures connected to their sharp threading end. The urethral stump suturing device at mid position enables linear arm movement (171) and suture needle rotation movement (172).

Figure 18:
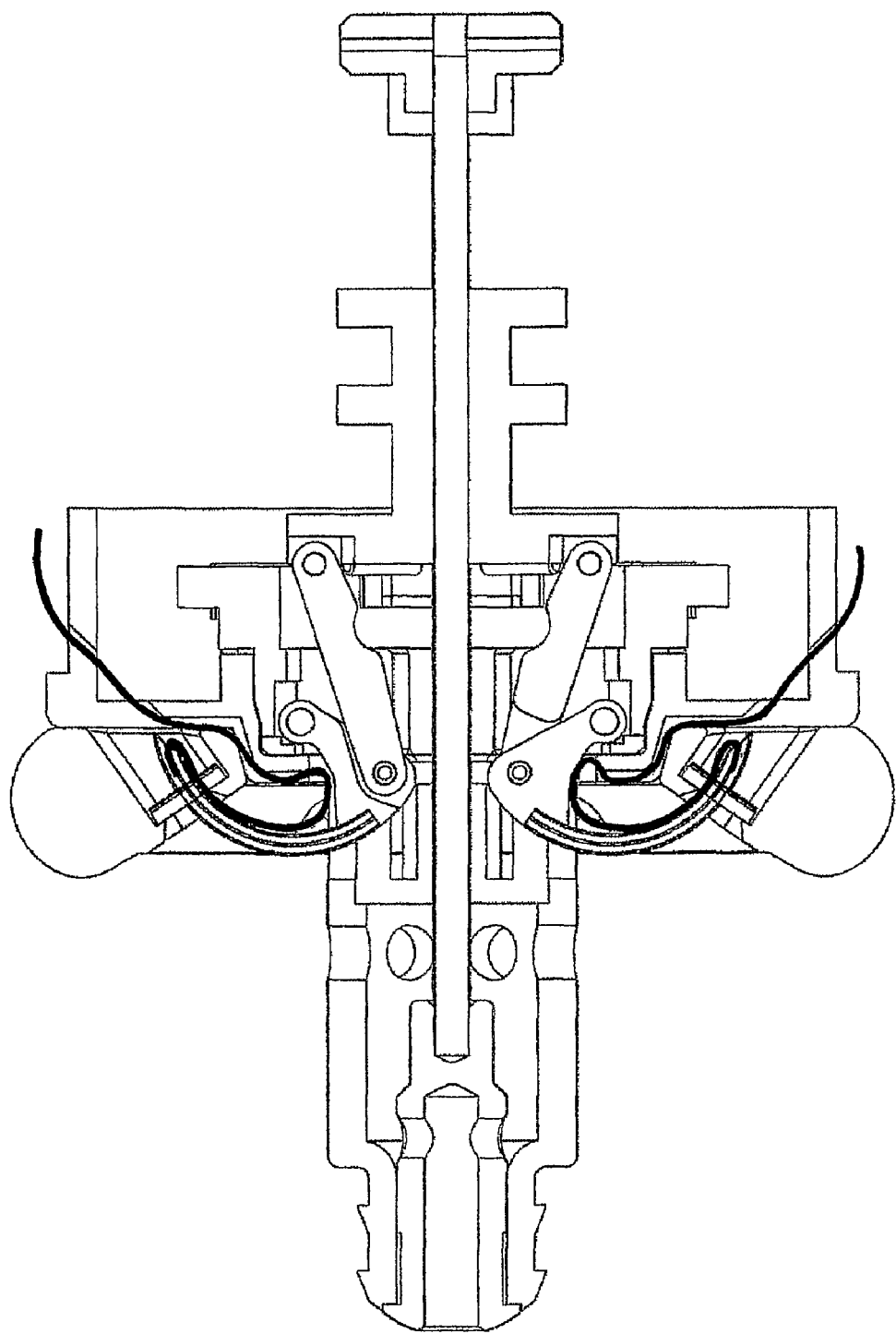
FIG. 18 schematically presents the urethral stump suturing device wherein the needles are at their most outward/rotated position.

Reference is now made to FIG. 18 schematically presenting the urethral stump suturing device wherein the needles are at their most outward/rotated position; the needles with the sutures have passed the tissue (not shown) and have entered the sutures capturing mechanisms.

Figure 19:
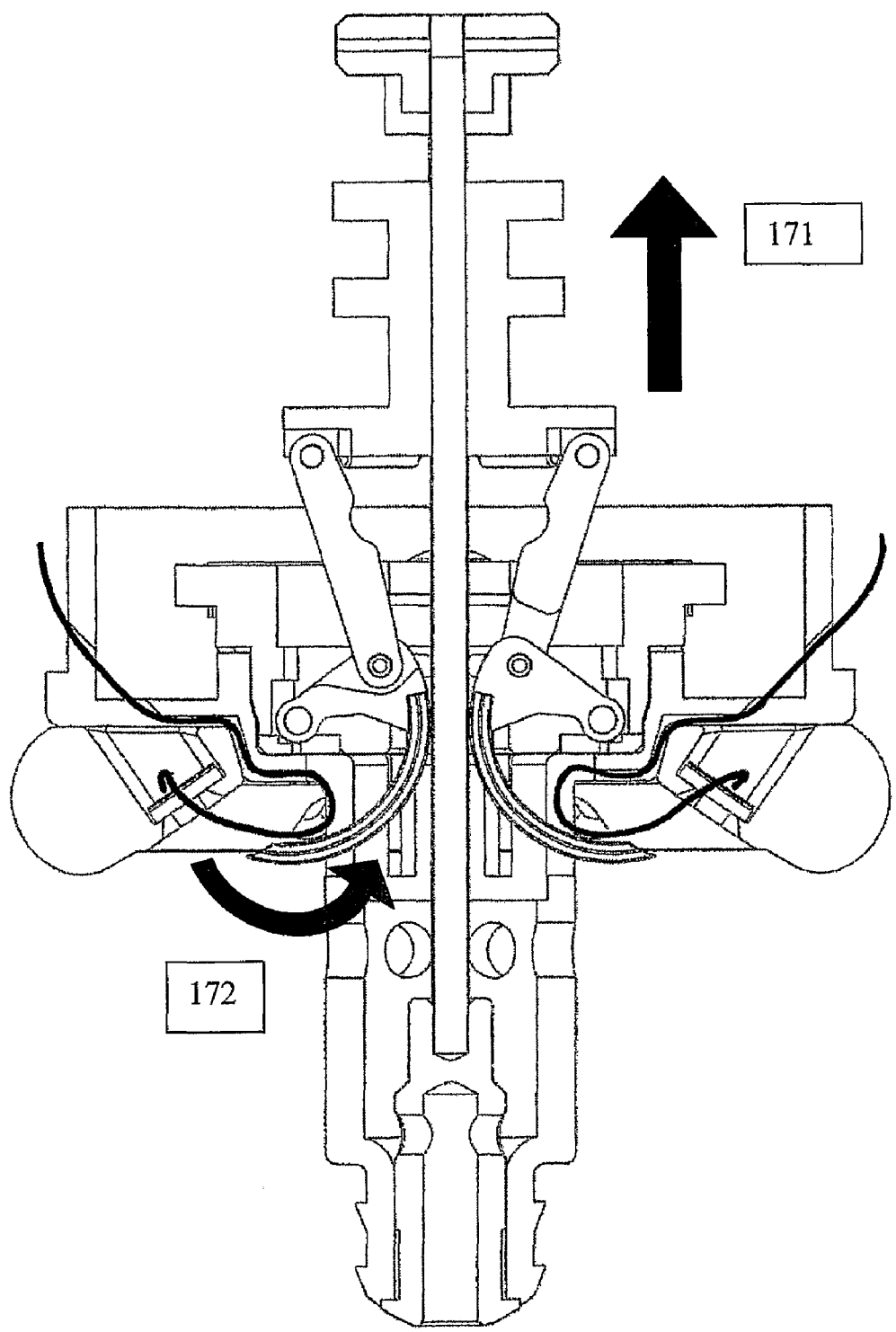
FIG. 19 schematically presents the urethral stump suturing device, wherein the needles are partially retracted following threading the sutures through the tissue into the sutures capturing mechanisms.

Reference is now made to FIG. 19 schematically presenting the urethral stump suturing device, wherein the needles are partially retracted following threading the sutures through the tissue into the sutures capturing mechanisms. The urethral stump suturing device enables linear arm movement (171) and suture needle rotation movement (172).

Figure 20:
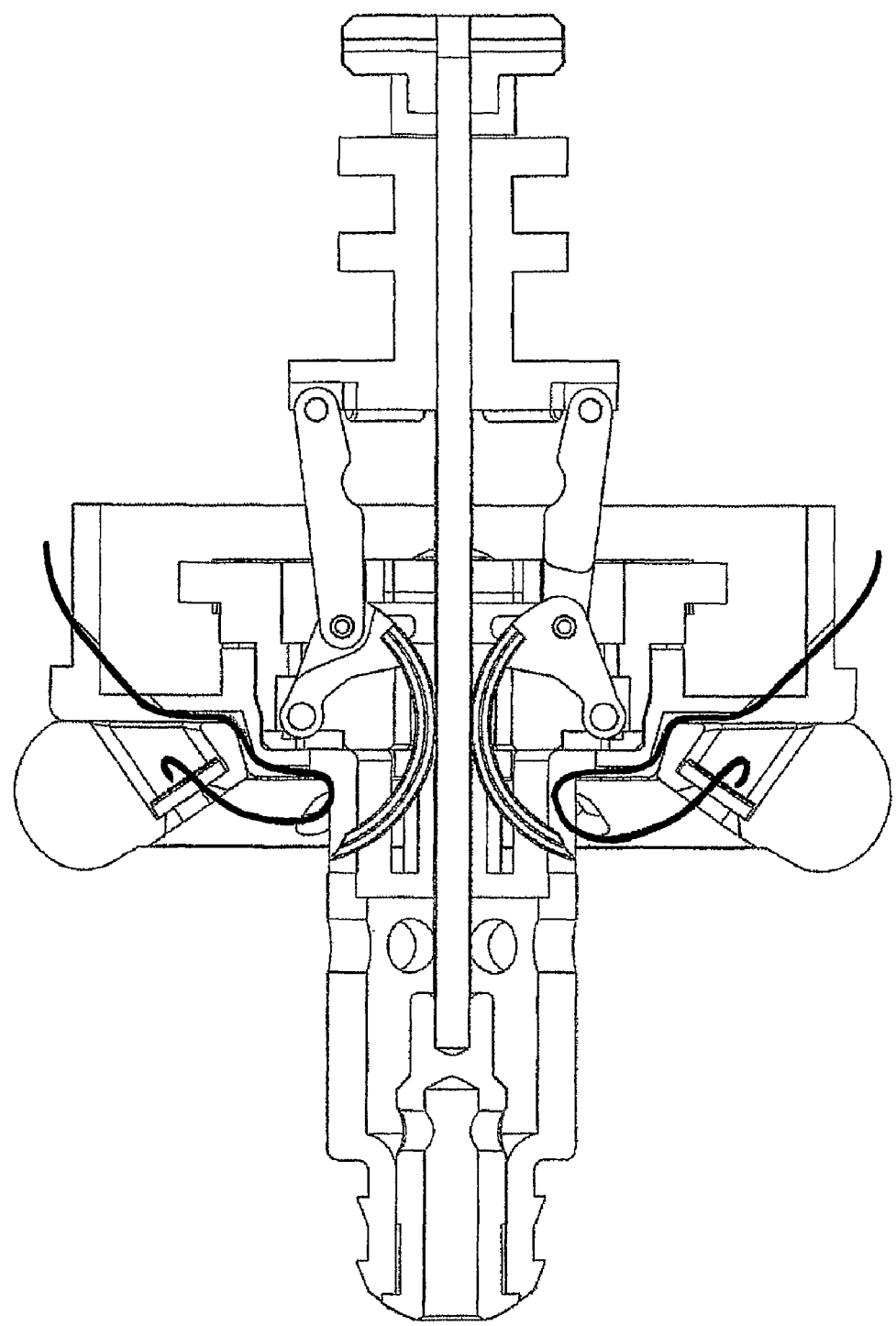
FIG. 20 schematically presents the urethral stump suturing device wherein the needles are fully retracted following threading the sutures.

Reference is now made to FIG. 20 schematically presenting the urethral stump suturing device wherein the needles are fully retracted following threading the sutures.

Figure 21:
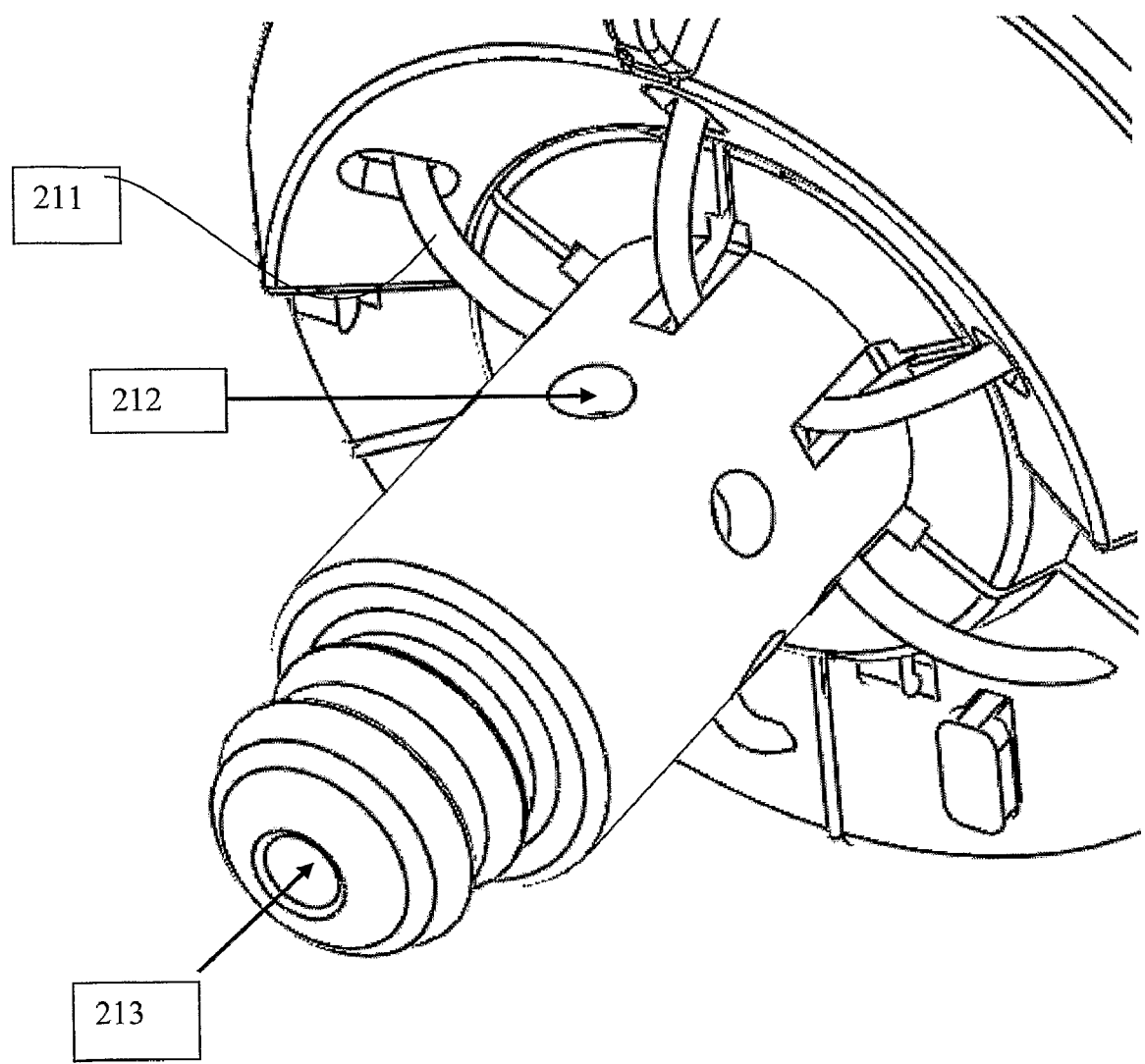
FIG. 21 schematically presents the suture capturing/locking ring according to another embodiment of the present invention.

Reference is now made to FIG. 21 schematically presenting the suture capturing/locking ring according to another embodiment of the present invention. The suture capturing/locking ring comprises six suture needles fully extracted (211), six suction/pressure holes for tissue positioning and holding (212) and air/fluid inlet/outlet supply the positioning/holding holes (213).

Figure 22A:
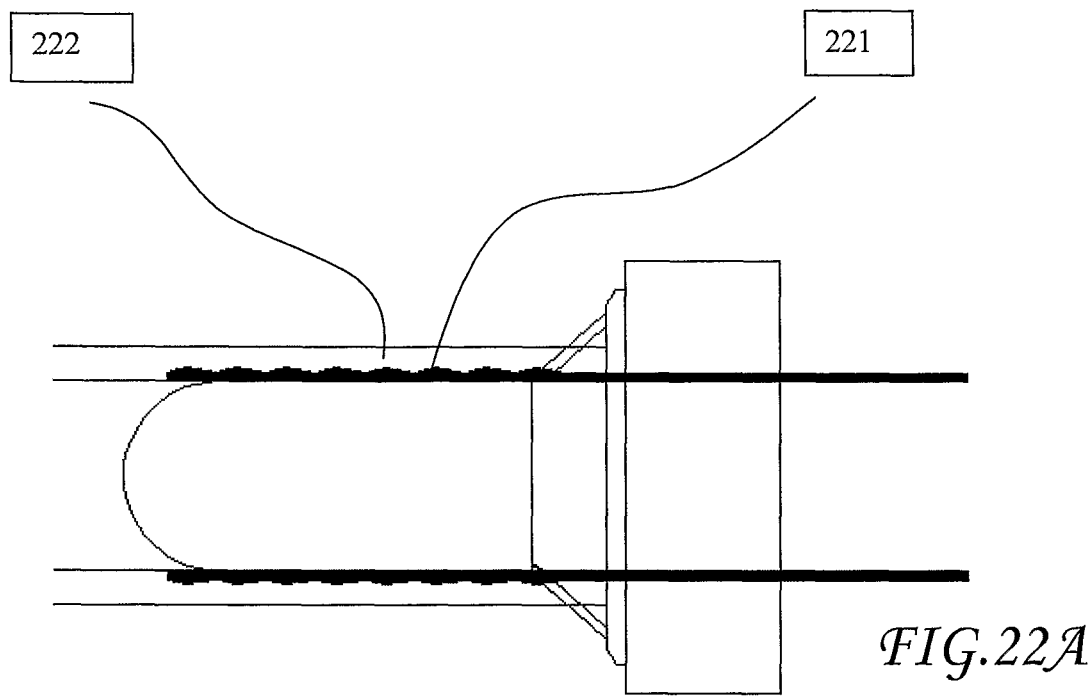
FIGS. 22A and 22B schematically present the single use feature of the device according to another optional embodiment of the mechanism.
Figure 22B:
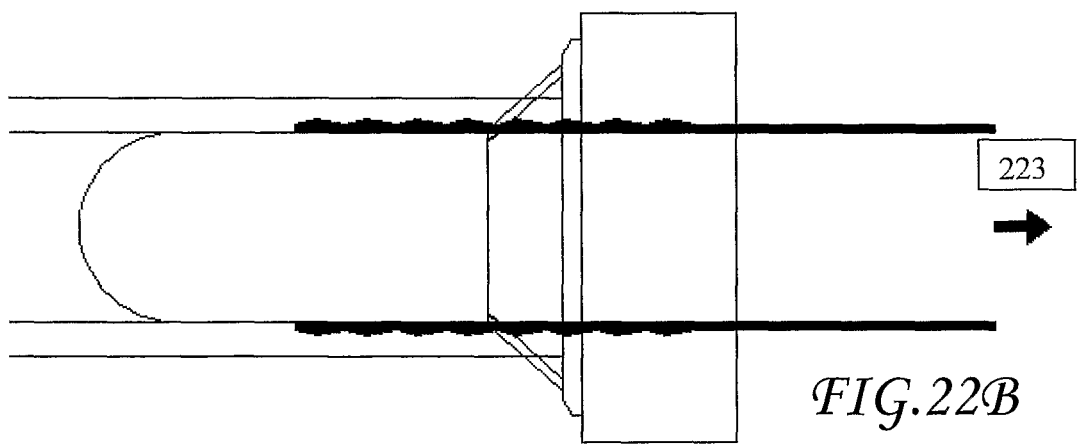

Reference is now made to FIGS. 22A and 22B schematically presenting the single use feature (221) of the device according to another optional embodiment of the mechanism. The strips are pulled out, enabling easier positioning of the urethral stump for suturing/threading. Each strip 3 to 6 is pulled out separately or all the strips are pulled out simultaneously. The urethral stump tissue (222) is also represented. The pull out is represented as 223.

Figure 23A:
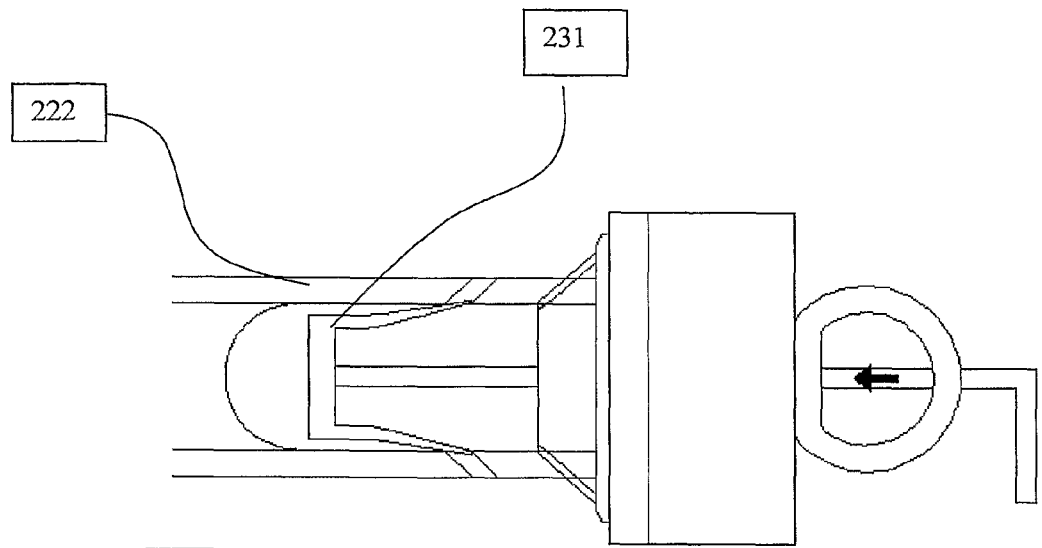
FIGS. 23A and 23B schematically present the flexible pull/push mechanism that enables easier positioning of the urethral stump for suturing/threading.
Figure 23B:
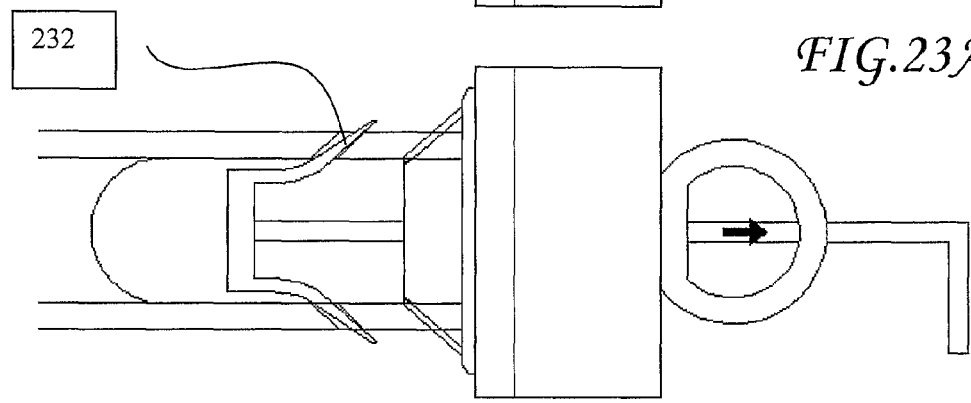
Figure 24A:
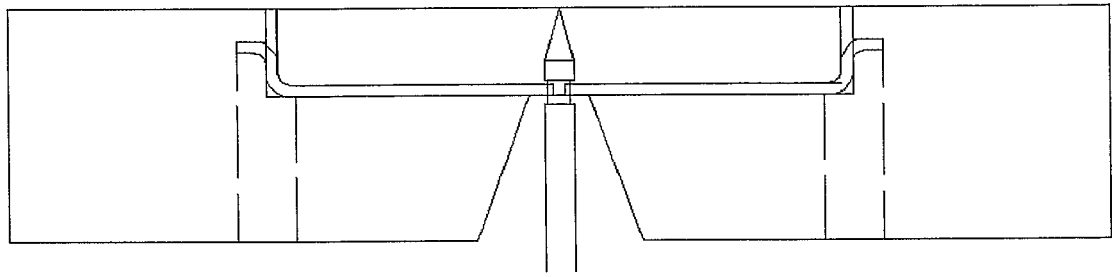
FIG. 24 schematically presents an option at which the rotating needle threads an anchor with a suture connected to it through the tissue.
Figure 24B:
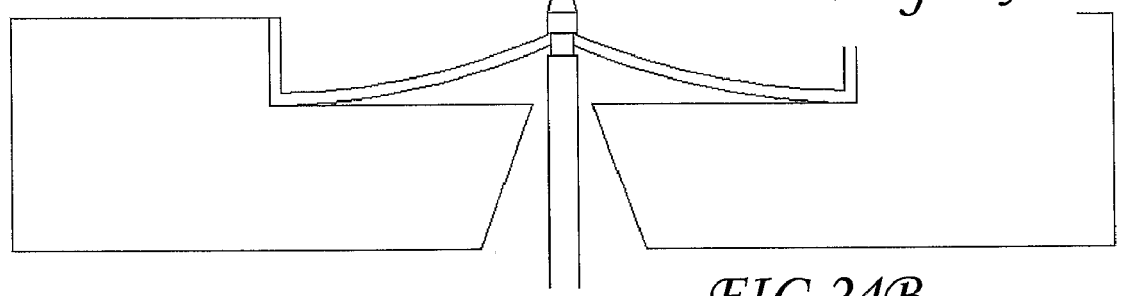
Figure 24C:
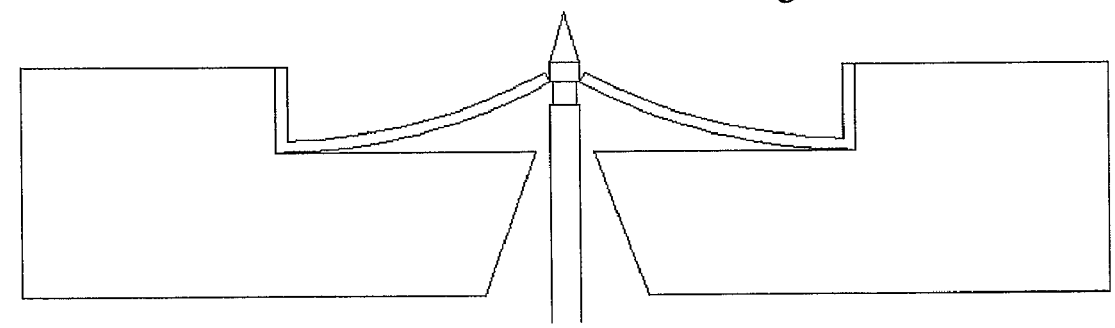
Figure 24D:
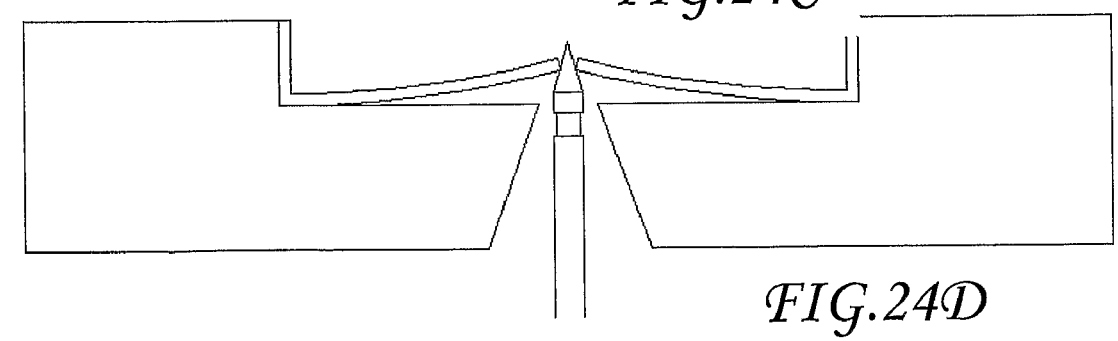

Reference is now made to FIGS. 23A and 23B schematically presenting the flexible pull/push mechanism (231) that enables easier positioning of the urethral stump for suturing/threading. The physician actuates this mechanism at his choice, until he is satisfied with the tissue position, for suturing according to another embodiment of the present invention. The ends of the mechanism are not sharp is illustrated in FIG. 23B, thus will not harm the tissue Reference is now made to FIG. 24 schematically presenting an option at which the rotating needle threads an anchor with a suture connected to it through the tissue. Following threading, the anchor locks to the suture locking ring.

Figure 25A:
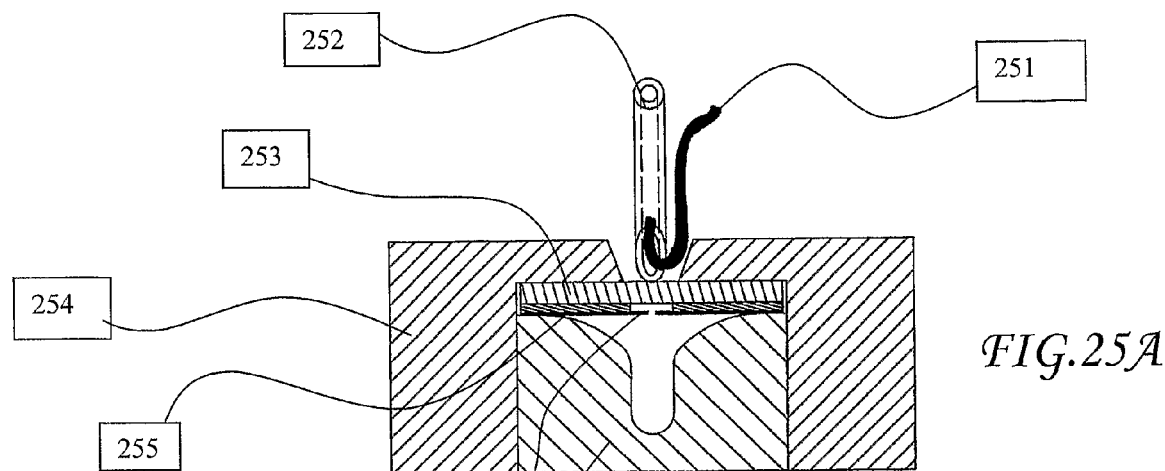
FIGS. 25A, 25B and 25C schematically present a cross section of locking mechanism of the capturing ring wherein 25A illustrates the step before the penetration, 25B the step wherein the penetration is complete and the needle (252) is completely extracted, and 25C the step wherein the suture (251) is captured.
Figure 25B:
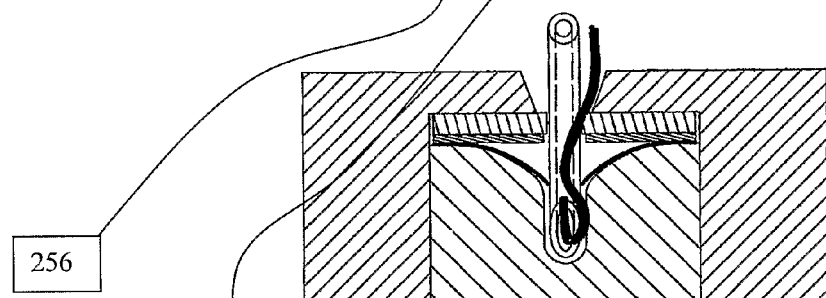
Figure 25C:
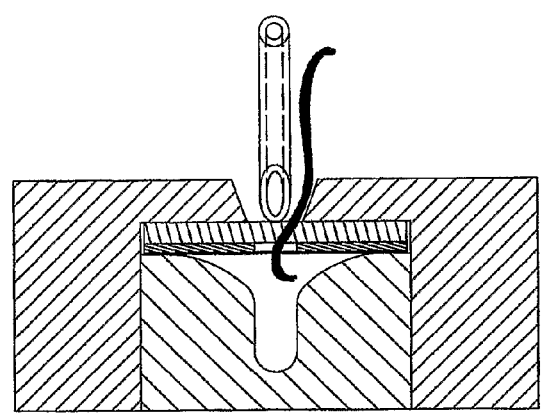

Reference is now made to FIGS. 25A, 25B and 25C schematically presenting a cross section of locking mechanism of the capturing ring wherein 25A illustrates the step before the penetration, 25B the step wherein the penetration is complete and the needle (252) is completely extracted, and 25C the step wherein the suture (251) is captured. The locking mechanism comprises a silicon plate/surface (253) which holds the suture while the needle retracts; housing (254); a thin rigid plate holding the silicon in place (255); a flexible thin plate used to capture the suture (256); and a structure used to limit the movement of the flexible thin plate (257).

The invention claimed is:

1. A method of performing a urethral-vesicle anastomosis, comprising:
   a. introducing a guiding catheter (3) into the urethra from the penis until it protrudes from the urethral stump;
   b. connecting said guiding catheter (3) to a suturing unit located at the end of said urethral stump suturing unit (Ia);
   c. retracting said catheter outwardly to position the tip of said urethral suturing unit (Ia) in the opening of the urethral stump;
   d. introducing said urethral suturing unit (Ia) into said urethral stump;
   e. positioning the urethral wall in accordance to the urethral stump suturing unit (Ia) in order to achieve an adequate piercing position;
   f. activating a piercing unit (10) from within said urethral suturing unit (Ia) and passing a plurality of suture needles through the urethral wall at positions radially equidistant about the urethral stump;
   g. contracting said positioning mechanism;
   h. removing said suture unit from said urethral stump;
   i. attaching said bladder neck suturing unit (Ib) to said urethral stump suturing unit (Ia) by means of a flexible crossbar (2);
   j. attaching the sutures to the needles of said piercing unit;
   k. inserting the bladder neck suturing unit (Ib) into the bladder's neck;
   l. performing said positioning and threading procedures by means of a bladder neck suturing unit (Ib) and passing the needles and sutures through the wall of said bladder neck;
   m. anchoring the needle or the suture anchored in a second needle/suture-anchoring ring;
   n. contracting the bladder neck positioning mechanism and removing the suture unit from the bladder;
   o. detaching said two suturing mechanisms from their sutures engagement rings and the crossbar (2) from the needle/suture-anchoring rings(14) and retracting through the wound;
   p. passing a Foley catheter (15) from the urethral opening through the engagement rings and captivated sutures, into the bladder, so as each of the anchoring rings is divided into a plurality of semicircular sections, especially two sections;
   q. retracting the same through the wound;
   r. inflating a balloon located at the end of said Foley catheter (15) being situated within said bladder;
   s. pulling said catheter outwardly from said penis, connecting said urethra stump and the bladder neck simultaneously; and t. providing said sutures drawn tight and tying the sutures manually.

2. The method of performing a urethral-vesicle anastomosis according to claim 1, comprising maintaining the posterior urethral wall intact, i.e. cutting through the anterior wall only.

3. The method of performing a urethral-vesicle anastomosis according to claim 1, comprising predetermining the number and the location of needled being operated in each set of needle insertion before or while the operation.

4. The method of performing a urethral-vesicle anastomosis according to claim 1, comprising positioning said needles in the one o'clock, three o'clock, the five o'clock, seven o'clock, nine o'clock and eleven o'clock positions.

5. The method of performing a urethral-vesicle anastomosis according to claim 1, comprising connecting each of said plurality of sutures to a needle in one suture unit and passing through a guiding notch in the outer circumference of said needle-anchoring ring.

* * * * *